United States Patent
Cooper et al.

(10) Patent No.: US 9,822,359 B1
(45) Date of Patent: Nov. 21, 2017

(54) METHOD OF TREATING NEUROLOGICAL DISORDERS USING LONG NON-CODING RNAS

(71) Applicants: Denise R. Cooper, St. Petersburg, FL (US); Cesario Borlongan, Tampa, FL (US); Paula Cole Bickford, Ruskin, FL (US); Niketa A. Patel, Land O'Lakes, FL (US); Lisa Gould, Warwick, RI (US)

(72) Inventors: Denise R. Cooper, St. Petersburg, FL (US); Cesario Borlongan, Tampa, FL (US); Paula Cole Bickford, Ruskin, FL (US); Niketa A. Patel, Land O'Lakes, FL (US); Lisa Gould, Warwick, RI (US)

(73) Assignees: University of South Florida, Tampa, FL (US); The United States of America as Represented by the Department of Veterans Affairs, Washington, DC (US)

( * ) Notice: Subject to any disclaimer, the term of this patent is extended or adjusted under 35 U.S.C. 154(b) by 174 days.

(21) Appl. No.: 14/602,945

(22) Filed: Jan. 22, 2015

Related U.S. Application Data

(60) Provisional application No. 61/930,353, filed on Jan. 22, 2014.

(51) Int. Cl.
| | | |
|---|---|---|
| *C12N 15/113* | (2010.01) | |
| *A61K 48/00* | (2006.01) | |
| *A61K 35/35* | (2015.01) | |

(52) U.S. Cl.
CPC ............ *C12N 15/113* (2013.01); *A61K 35/35* (2013.01); *A61K 48/00* (2013.01)

(58) Field of Classification Search
CPC ....... A61K 35/35; A61K 48/00; C12N 15/113
See application file for complete search history.

(56) References Cited

PUBLICATIONS

Tajiri et al. (J. Neurosci., Jan. 1, 2014, 34(1):313-326).*
Chang et al. (Neurodegenerative Diseases 2014; 13:99-102, published online Oct. 23, 2013).*
Gutschner et al. (J. Mol. Med. (2013) 91:791-801).*
Baker, Nature Methods (2011) 8(5):379-383).*
Enerback, S., The Origins of Brown Adipose Tissue. Clinical Implications of Basic Research, The New England Journal of Medicine, 360;19. May 7, 2009. pp. 2021-2023.
Gesta, et al., Developmental Origin of Fat: Tracking Obesity to Its Source. Cell 131, Oct. 19, 2007. pp. 242-256.
Wagner, et al., Comparative Characteristics of Mesenchymal Stem Cells from Human Bone Marrow, Adipose Tissue, and Umbilical Cord Blood. Experimental Hematology 33 (2005) 1402-1416.
Acosta SA, Tajiri N, Shinozuka K, Ishikawa H, Grimmig B, Diamond D, Sanberg PR, Bickford PC, Kaneko Y, Borlongan CV. Long-term upregulation of inflammation and suppression of cell proliferation in the brain of adult rats exposed to traumatic brain injury using the controlled cortical impact model. PLoS One, vol. 8, Issue 1, Jan. 2013, pp. 1-8.
Ajmo CT Jr, Vernon DO, Collier L, Hall AA, Garbuzova-Davis S, Willing A, Pennypacker KR. The spleen contributes to stroke-induced neurodegeneration. J Neurosci Res. vol. 86, Issue 10, Aug. 1, 2008, pp. 1-14.
Arslan F, Lai RC, Smeets MB, Akeroyd L, Choo A, Aguor EN, Timmers L, van Rijen HV, Doevendans PA, Pasterkamp G, Lim SK, de Kleijn DP. Mesenchymal stem cell-derived exosomes increase ATP levels, decrease oxidative stress and activate PI3K/Akt pathway to enhance myocardial viability and prevent adverse remodeling after myocardial ischemia/reperfusion injury. Stem Cell Res. vol. 10, 2013, pp. 301-312.
Baek SJ, Kang SK, Ra JC. In vitro migration capacity of human adipose tissue-derived mesenchymal stem cells reffects their expression of receptors for chemokines and growth factors. Exp Mol Med, vol. 43, No. 10, Oct. 2011, pp. 596-603.
Bernard D, Prasanth KV, Tripathi V, Colasse S, Nakamura T, Xuan Z, Zhang MQ, Sedel F, Jourdren L, Coulpier F, Triller A, Spector DL, Bessis A. A long nuclear-retained non-coding RNA regulates synaptogenesis by modulating gene expression. The EMBO Journal, vol. 29, 2010, pp. 3082-3093.
Bjorklund LM, Sa'nchez-Pemaute R, Chung S, Andersson T, Chen IY, Mc- Naught KS, Brownell AL, Jenkins BG, Wahlestedt C, Kim KS, Isacson O. Embryonic stem cells develop into functional dopaminergic neurons after transplantation in a Parkinson rat model. Proc Natl Acad Sci. vol. 99, No. 4, Feb. 19, 2002, pp. 2344-2349.
Bjugstad KB, Teng YD, RedmondDEJr, Elsworth JD, Roth RH, Cornelius SK, Snyder EY, Sladek JR Jr. Human neural stem cells migrate along the nigrostriatal pathway in a primate model of Parkinson's disease. Exp Neurol, vol. 211, Issue 2, 2008 pp. 362-369.
Blaber SP, Webster RA, Hill CJ, Breen EJ, Kuah D, Vesey G, Herbert BR. Analysis of in vitro secretion profiles from adipose-derived cell populations. J Transl Med, vol. 10, Issue 172, 2012, pp. 1-16.
Boddington S, Henning TD, Sutton EJ, Daldrup-Link HE. Labeling stem cells with fluorescent dyes for non-invasive detection with optical imaging. J Vis Exp (14):pii:686.

(Continued)

*Primary Examiner* — J. E. Angell
(74) *Attorney, Agent, or Firm* — Michele L. Lawson; Smith & Hopen, P.A.

(57) ABSTRACT

A method of treating traumatic brain injury (TBI) and other neurological disorders is presented herein. Both conditioned media (CM) containing long non-coding RNAs such as NEAT1 (nuclear enriched abundant transcript 1) and MALAT1 (metastasis associated lung adenocarcinoma transcript 1) as well as human adipose-derived stem cells (hADSCs) themselves (Tx), when administered at least 3 hours post injury, were found to significantly ameliorate motor and cognitive functions in young, but not aged, mice undergoing TBI. Significant reduction in cortical damage and hippocampal cell loss was observed in both Tx and CM groups in young rats, whereas less neuroprotection was detected in the aged rats and mainly in the Tx group but not the CM group, which may in part result from decreased homing of the cells to the spleen.

5 Claims, 12 Drawing Sheets

(56) References Cited

PUBLICATIONS

Bond CS, Fox AH, Paraspeckles: nuclear bodies built on long noncoding RNA. J Cell Biol 186; 5, Aug. 31, 2009, pp. 637-644.
Borlongan CV, Sanberg PR (1995) Elevated body swing test: a new behavioral parameter for rats with 6-hydroxydopamine-induced hemiparkinsonism. J Neurosci 15:5372-5378.
Borlongan CV, Hida H, Nishino H (1998) Early assessment of motor dysfunctions aids in successful occlusion of the middle cerebral artery. Neuroreport 9:3615-3621.
Carlson ME, Conboy IM (2007) Loss of stem cell regenerative capacity within aged niches. Aging Cell 6:371-382.
Cho YJ, Song HS, Bhang S, Lee S, Kang BG, Lee JC, An J, Cha CI, Nam DH, Kim BS, JooKM (2012) Therapeutic effects of human adipose stem cell conditioned medium on stroke. J Neurosci Res 90:1794-1802.
Clarkson ED (2001) Fetal tissue transplantation for patients with Parkinson's disease: a database of published clinical results. Drugs Aging 18:773-785.
Clemson CM, Hutchinson JN, Sara SA, Ensminger AW, Fox AH, Chess A, Lawrence JB (2009) An architectural role for a nuclear noncoding RNA: NEAT1 RNA is essential for the structure of paraspeckles. Mol Cell 33: 717-726.
Conboy IM, Conboy MJ, Wagers AJ, Girma ER, Weissman IL, Rando TA (2005) Rejuvenation of aged progenitor cells by exposure to a young systemic environment. Nature 433:760-764.
Darkazalli A, Levenson CW (2012) Tracking stem cell migration and survival in brain injury: current approaches and future prospects. Histol Histopathol 27:1255-1261.
Derrien T, Johnson R, Bussotti G, Tanzer A, Djebali S, Tilgner H, Guernec G, Martin D, Merkel A, Knowles DG, Lagarde J, Veeravalli L, Ruan X, Ruan Y, Lassmann T, Carninci P, Brown JB, Lipovich L, Gonzalez JM, Thomas M, Davis CA, Shiekhattar R, Gingeras TR, Hubbard TJ, Notredame C, Harrow J, Guigo' R (2012) The GENCODE v7 catalog of human long noncoding RNAs: analysis of their gene structure, evolution, and expression. Genome Res 22:1775-1789.
Detante O, Moisan A, Dimastromatteo J, Richard MJ, Riou L, Grillon E, Barbier E, Desruet MD, De Fraipont F, Segebarth C, Jaillard A, Hommel M, Ghezzi C, Remy C (2009) Intravenous administration of 99mTc-HMPAO-labeled human mesenchymal stem cells after stroke: in vivo imaging and biodistribution. Cell Transplant 18:1369-1379.
Egashira Y, Sugitani S, Suzuki Y, Mishiro K, Tsuruma K, Shimazawa M, Yoshimura S, Iwama T, Hara H (2012) The conditioned medium of murine and human adipose-derived stem cells exerts neuroprotective effects against experimental stroke model. Brain Res 1461:87-95.
Faul M, Xu L, Wanld MM, Coronado VG (2010) Traumatic brain injury in the United States: emergency department visits, hospitalizations, and deaths. Atlanta GA: Centers for Disease Control and Prevention, National Center for Injury Prevention and Control.
Fox AH, Lamond AI (2010) Paraspeckles. Cold Spring Harbor Perspect Biol 2:a000687.
Fraser JK, Wulur I, Alfonso Z, Hedrick MH (2006) Fat tissue: an underappreciated source of stem cells for biotechnology. Trends Biotechnol 24;4 : 150-154.
Galindo LT, Filippo TR, Semedo P, Ariza CB, Moreira CM, Camara NO, Porcionatto MA (2011) Mesenchymal stem cell therapy modulates the inflammatory response in experimental traumatic brian injury. Neurol Res Int 2011:564089.
Glover LE, Tajiri N, Lau T, Kaneko Y, van Loveren H, Borlongan CV (2012) Immediate, but not delayed, microsurgical skull reconstruction exacerbates brain damage in experimental traumatic brain injury model. PLoS One 7:e33646.
Harting MT, Sloan LE, Jimenez F, Baumgartner J, Cox CS Jr (2009) Subacute neural stem cell therapy for traumatic brain injury. J Surg Res 153: 188-194.
Hawkins BE, Cowart JC, Parsley MA, Capra BA, Eidson KA, Hellmich HL, Dewitt DS, Prough DS (2013) Effects of trauma, hemorrhage and resuscitation in aged rats. Brain Res 1496:28-35.
Hayashi T, Kaneko Y, Yu S, Bae E, Stahl CE, Kawase T, van Loveren H, Sanberg PR, Borlongan CV (2009) Quantitative analyses of matrix metalloproteinase activity after traumatic brain injury in adult rats. Brain Res 1280:172-177.
Ibrahim AG, Raisman G, Li Y (2009) Permanent loss of fore-paw grasping requires complete deprivation of afferent input from a minimum of four dorsal roots of the rat brachial plexus. Exp Neurol 215:142-145.
Ikegame Y, Yamashita K, Hayashi S, Mizuno H, Tawada M, You F, Yamada K, Tanaka Y, Egashira Y, Nakashima S, Yoshimura S, Iwama T (2011) Comparison of mesenchymal stem cells from adipose tissue and bone marrow for ischemic stroke therapy. Cytotherapy 13:675-685.
Isacson O, Costantini L, Schumacher JM, Cicchetti F, Chung S, Kim K (2001) Cell implantation therapies for Parkinson's disease using neural stem, transgenic or xenogeneic donor cells. Parkinsonism Relat Disord 7:205-212.
Jang YY, Ye Z, Cheng L (2011) Molecular imaging and stem cell research. Mol Imaging 10:111-122. Medline Katsuda T, Tsuchiya R, Kosaka N, Yoshioka Y, Takagaki K, Oki K, Takeshita F, Sakai Y, Kuroda M, Ochiya T (2013) Human adipose tissue-derived mesenchymal stem cells secrete functional neprilysin-bound exosomes. Sci Rep 3:1197.
Kim WS, Park BS, Sung JH, Yang JM, Park SB, Kwak SJ, Park JS (2007) Wound healing effect of adipose-derived stem cells: a critical role of secretory factors on human dermal fibroblasts. J Dermatol Sci 48:15-24.
Lee P, Kim J, Williams R, Sandhir R, Gregory E, Brooks WM, Berman NE (2012) Effects of aging on blood brain barrier and matrix metalloproteases following controlled cortical impact in mice. Exp Neurol 234:50-61.
Lefebvre JS, Maue AC, Eaton SM, Lanthier PA, Tighe M, Haynes L (2012) The aged microenvironment contributes to the age-related functional defects of CD4 T cells in mice. Aging Cell 11:732-740.
Lendeckel S, Jodicke A, Christophis P, Heidinger K, Wolff J, Fraser JK, Hedrick MH, Berthold L, Howaldt HP (2004) Autologous stem cells (adipose) and fibrin glue used to treat widespread traumatic calvarial defects: case report J Craniomaxillofac Surg 32:370-373.
Li M, Li F, Luo C, Shan Y, Zhang L, Qian Z, Zhu G, Lin J, Feng H (2011) Immediate splenectomy decreases mortality and improves cognitive function of rats after severe traumatic brain injury. J Trauma 71:141-147.
Lindvall O, Brundin P, Widner H, Rehncrona S, Gustavii B, Frackowiak R, Leenders KL, Sawle G, Rothwell JC, Marsden CD, Bjorkland A (1990) Grafts of fetal dopamine neurons survive and improve motor function in Parkinson's disease. Science 247:574-577.
Liu YP, Lang BT, Baskaya MK, Dempsey RJ, Vemuganti R (2009) The potential of neural stem cells to repair stroke-induced brain damage. Acta Neuropathol 117:469-480.
Mahmood A, Lu D, Lu M, Chopp M (2003) Treatment of traumatic brain injury in adult rats with intravenous administration of human bone marrow stromal cells. Neurosurgery 53:697-702; discussion 702-703.
McDonald KG, Leach MR, Huang C, Wang C, Newberry RD (2011) Aging impacts isolated lymphoid follicle development and function. Immunity Ageing 8:1.
Mercer TR, Mattick JS (2013) Structure and function of long noncoding RNAs in epigenetic regulation. Nat Struct Mol Biol 20:300-307.
Michalet X, Pinaud FF, Bentolila LS, Tsay JM, Doose S, Li JJ, Sundaresan G, Wu AM, Gambhir SS, Weiss S (2005) Quantum dots for live cells, in vivo imaging, and diagnostics. Science 307:538-544.
Mizuno H, Tobita M, Uysal AC (2012) Concise review: adipose-derived stem cells as a novel tool for future regenerative medicine. Stem Cells 30:804-810.

(56) References Cited

OTHER PUBLICATIONS

Muraoka K, Shingo T, Yasuhara T, Kameda M, Yuen Wj, Uozumi T, Matsui T, Miyoshi Y, Date I (2008) Comparison of the therapeutic potential of adult and embryonic neural precursor cells in a rat model of Parkinson disease. J Neurosurg 108:149-159.

Naganuma T, Hirose T (2013) Paraspeckle formation during the biogenesis of long non-coding RNAs. RNA Biol 10(8).

Nakagawa S, Hirose T (2012) Paraspeckle nuclear bodies—useful uselessness? Cell Mol Life Sci 69:3027-3036.

Qi JH, Ebrahem Q, Moore N, Murphy G, Claesson-Welsh L, Bond M, Baker A, Anand-Apte B (2003) A novel function for tissue inhibitor of metalloproteinases-3 (TIMP3): inhibition of angiogenesis by blockage of VEGF binding to VEGF receptor-2. Nat Med 9:407-415.

Ribeiro CA, Fraga JS, Graos M, Neves NM, Reis RL, Gimble JM, Sousa N, Salgado AJ (2012) The secretome of stem ells isolated from the adipose tissue and Wharton jelly acts differently on central nervous system derived cell populations. Stem Cell Res Ther 3:18.

Sasaki YT, Ideue T, Sano M, Mituyama T, Hirose T (2009) MENepsilon/ beta noncoding RNAs are essential for structural integrity of nuclear paraspeckles. Proc Natl Acad Sci U S A 106:2525-2530.

Singer NG, Caplan AI (2011) Mesenchymal stem cells: mechanisms of inflammation. Annu Rev Pathol 6:457-478.

SolantoMV (1984) Neuropharmacological basis of stimulant drug action in attention deficit disorder with hyperactivity: a review and synthesis. Psychol Bull 95:387-409.

Spadaro PA, Bredy TW (2012) Emerging role of non-coding RNA in neural plasticity, cognitive function, and neuropsychiatric disorders. Front Genet 3:132.

Sugiyama T, Kuroda S, Osanai T, Shichinohe H, Kuge Y, Ito M, Kawabori M, Iwasaki Y (2011) Near-infrared fluorescence labeling allows noninvasive tracking of bone marrow stromal cells transplanted into rat infarct brain. Neurosurgery 68:1036-1047; discussion 1047.

Sun J, Zhou H, Deng Y, Zhang Y, Gu P, Ge S, Fan X (2012) Conditioned medium from bone marrow mesenchymal stem cells transiently retards osteoblast differentiation by downregulating runx2. Cells Tissues Organs 196:510-522.

Ushiki T, Kizaka-Kondoh S, Ashihara E, Tanaka S, Masuko M, Hirai H, Kimura S, Aizawa Y, Maekawa T, HiraokaM (2010) Noninvasive tracking of donor cell homing by near-infrared fluorescence imaging shortly after bone marrow transplantation. PLoS One 5:e11114.

Vendrame M, Gemma C, Pennypacker KR, Bickford PC, Davis Sanberg C, Sanberg PR, Willing AE (2006) Cord blood rescues stroke-induced changes in splenocyte phenotype and function. Exp Neurol 199:191-200.

Vorhees CV, Williams MT (2006) Morris water maze: procedures for assessing spatial and related forms of learning and memory. Nat Protoc 1:848-858.

Walker PA, Shah SK, Harting MT, Cox CS Jr (2009) Progenitor cell therapies for traumatic brain injury: barriers and opportunities in translation. Dis Model Mech 2:23-38.

Walker PA, Shah SK, Jimenez F, GerberMH,Xue H, Cutrone R, Hamilton JA, Mays RW, Deans R, Pati S, Dash PK, Cox CS Jr (2010) Intravenous multipotent adult progenitor cell therapy for traumatic brain injury: preserving the blood brain barrier via an interaction with splenocytes. Exp Neurol 225:341-352.

Wapinski O, Chang HY (2011) Long noncoding RNAs and human disease. Trends Cell Biol 21:354-361.

Xue S, Zhang HT, Zhang P, Luo J, Chen ZZ, Jang XD, Xu RX (2010) Functional endothelial progenitor cells derived from adipose tissue show beneficial effect on cell therapy of traumatic brain injury. Neurosci Lett 473: 186-191.

Yang M, Donaldson AE, Jiang Y, Iacovitti L (2003) Factors influencing the differentiation of dopaminergic traits in transplanted neural stem cells. Cell Mol Neurobiol 23:851-864.

Yao J, Jiang SL, Liu W, Liu C, Chen W, Sun L, Liu Ky, Jia ZB, Li RK, Tian H (2012) Tissue inhibitor of matrix metalloproteinase-3 or vascular endothelial growth factor transfection of aged human mesenchymal stem cells enhances cell therapy after myocardial infarction. Rejuvenation Res 15: 495-506.

Yu S, Kaneko Y, Bae E, Stahl CE, Wang Y, van Loveren H, Sanberg PR, Borlongan CV (2009) Severity of controlled cortical impact traumatic brain injury in rats and mice dictates degree of behavioral deficits. Brain Res 1287:157-163.

Zhang B, Arun G, Mao YS, Lazar Z, Hung G, Bhattacharjee G, Xiao X, Booth CJ, Wu J, Zhang C, Spector DL (2012) The lncRNA Malat1 is dispensable for mouse development but its transcription plays a cis-regulatory role in the adult. Cell Rep 2:111-123.

\* cited by examiner

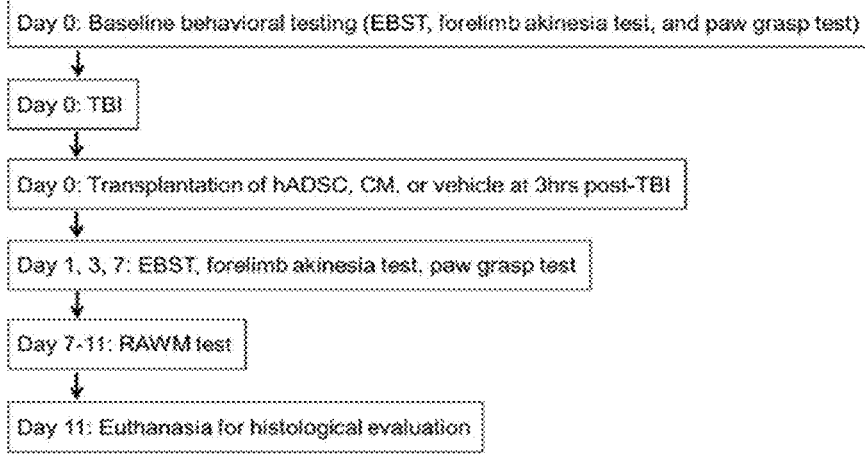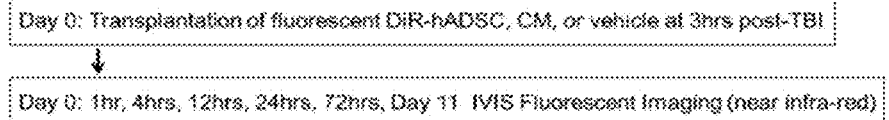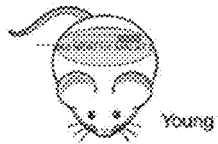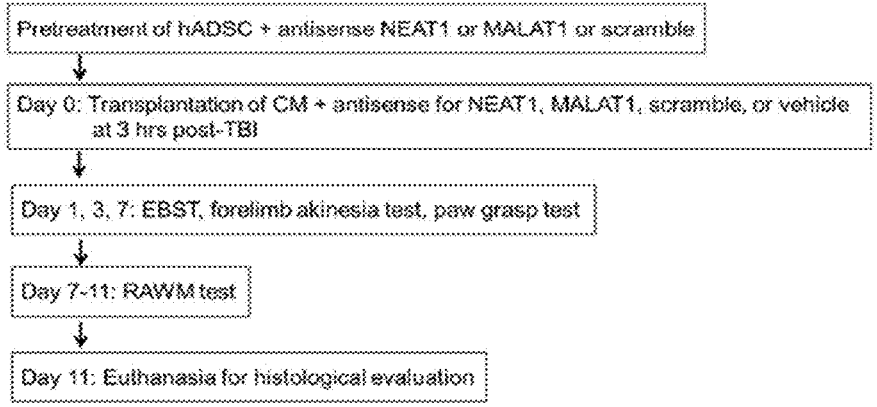
*Figure 1*

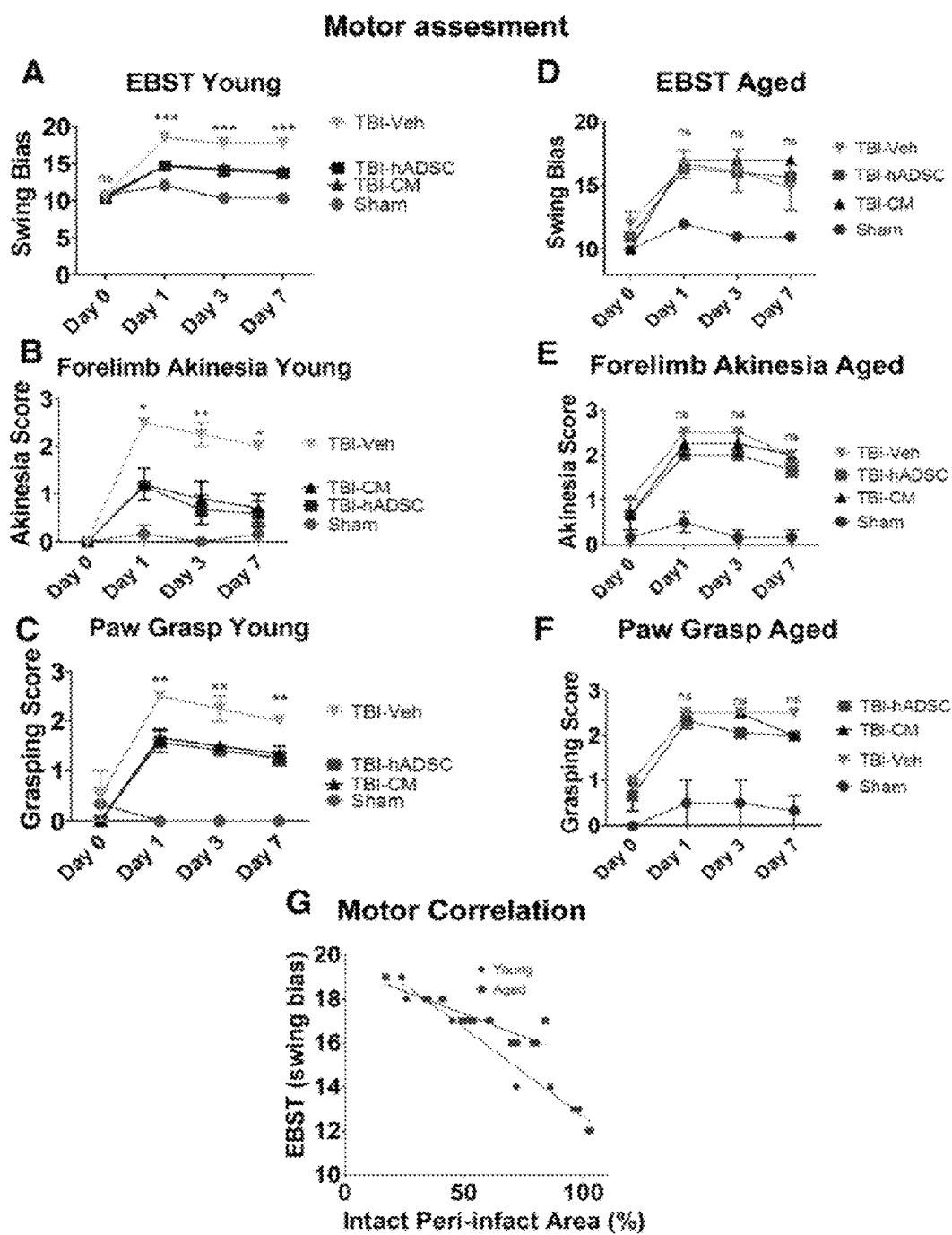
Figure 2A-G

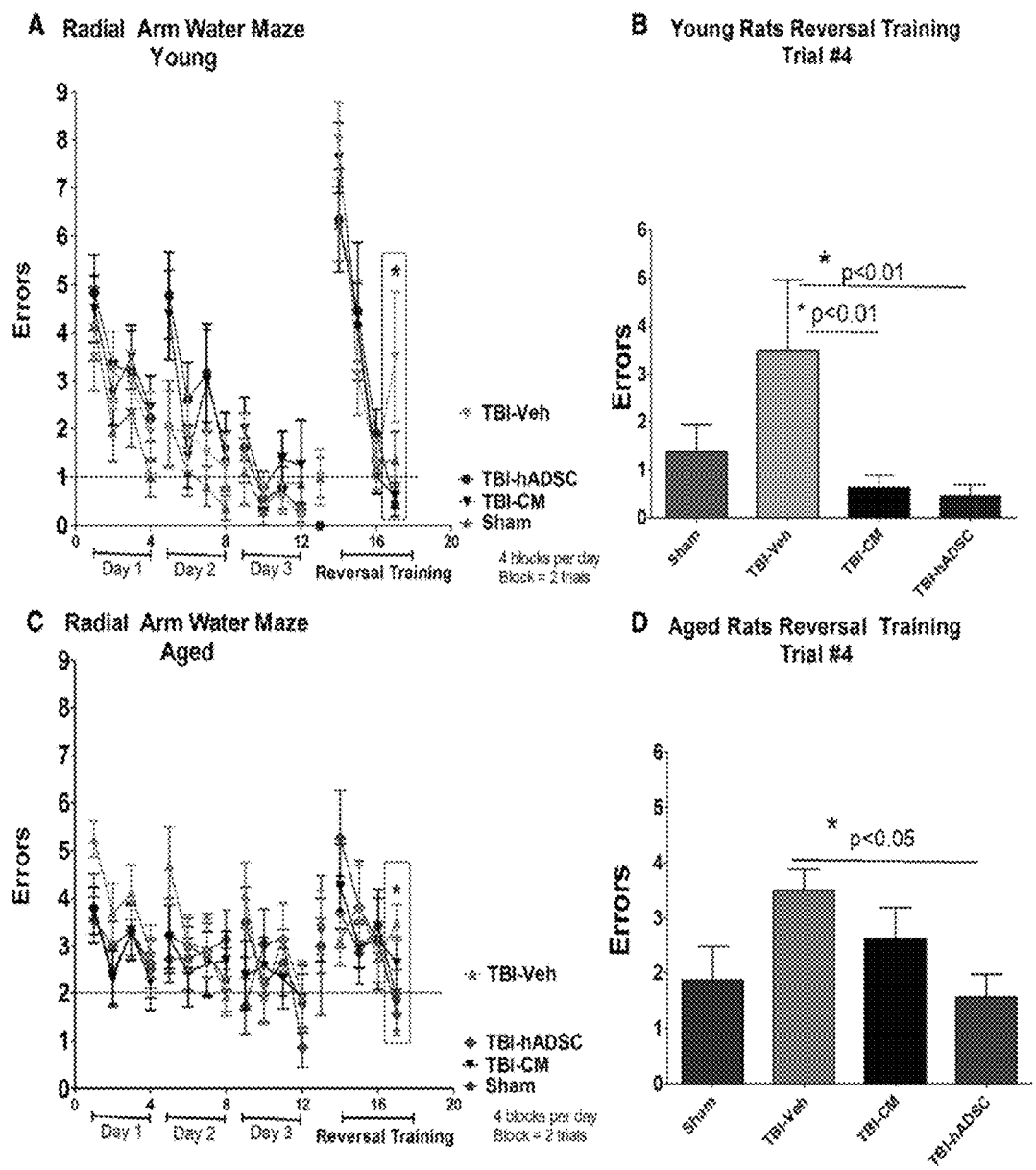
Figure 3A-D

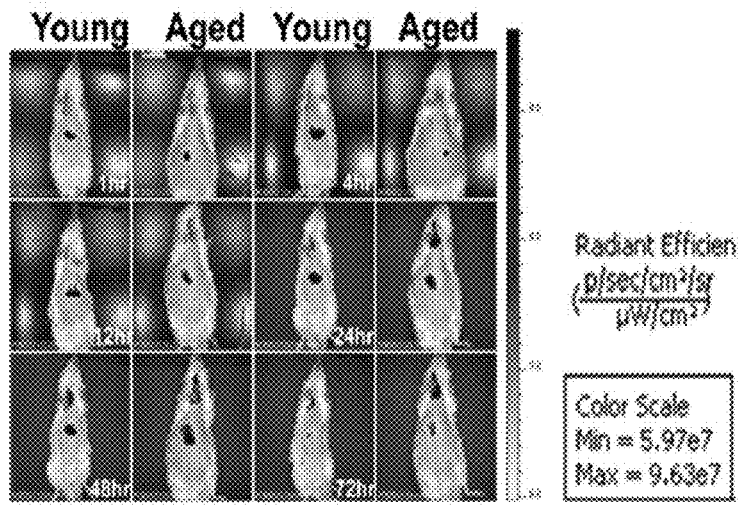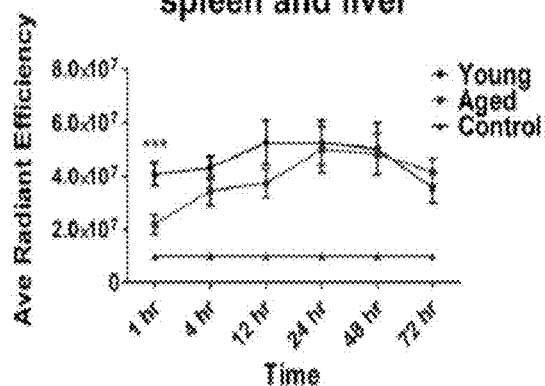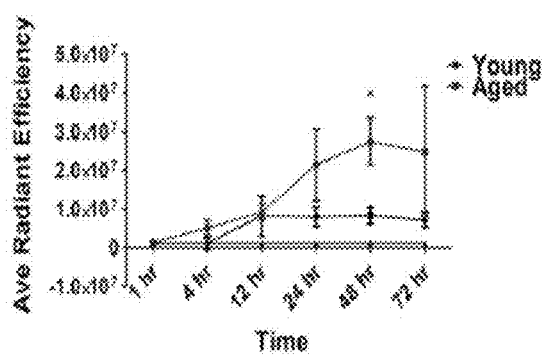
Figure 4A-C

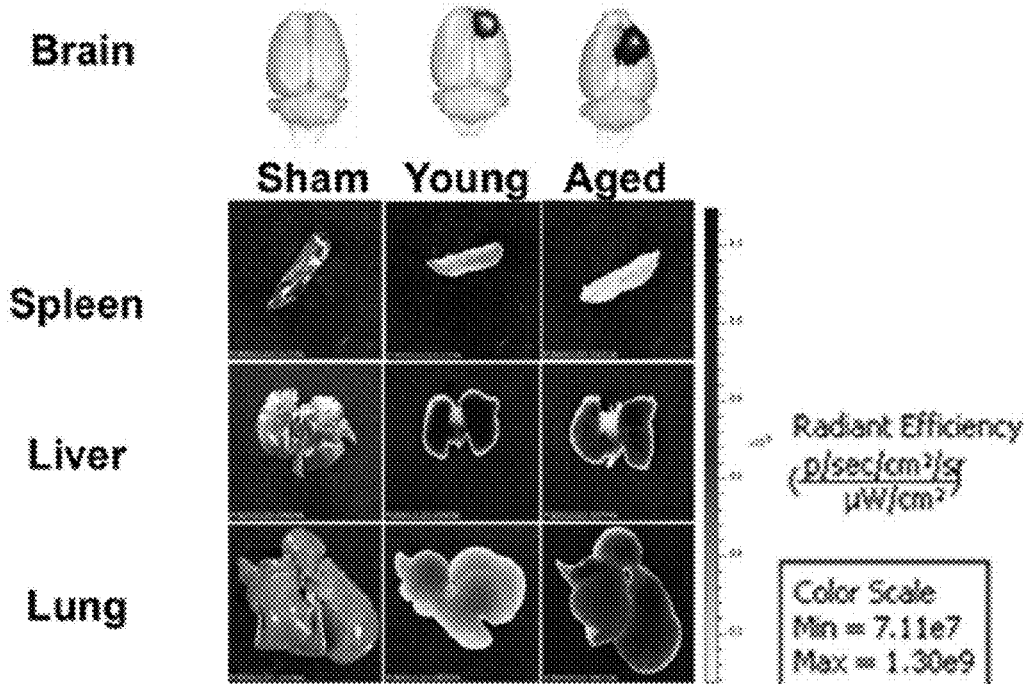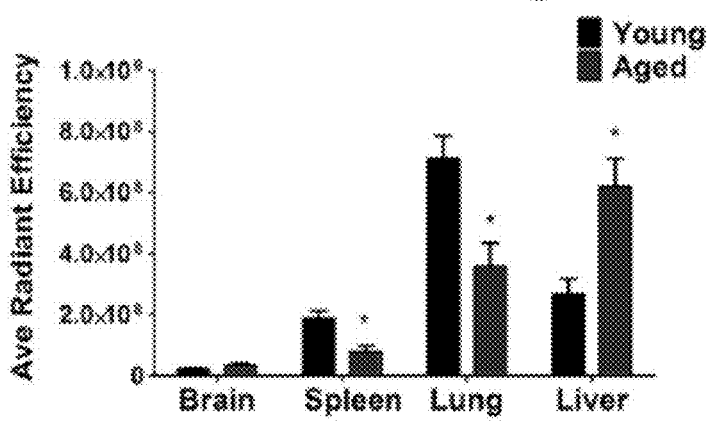
Figure 4D-E

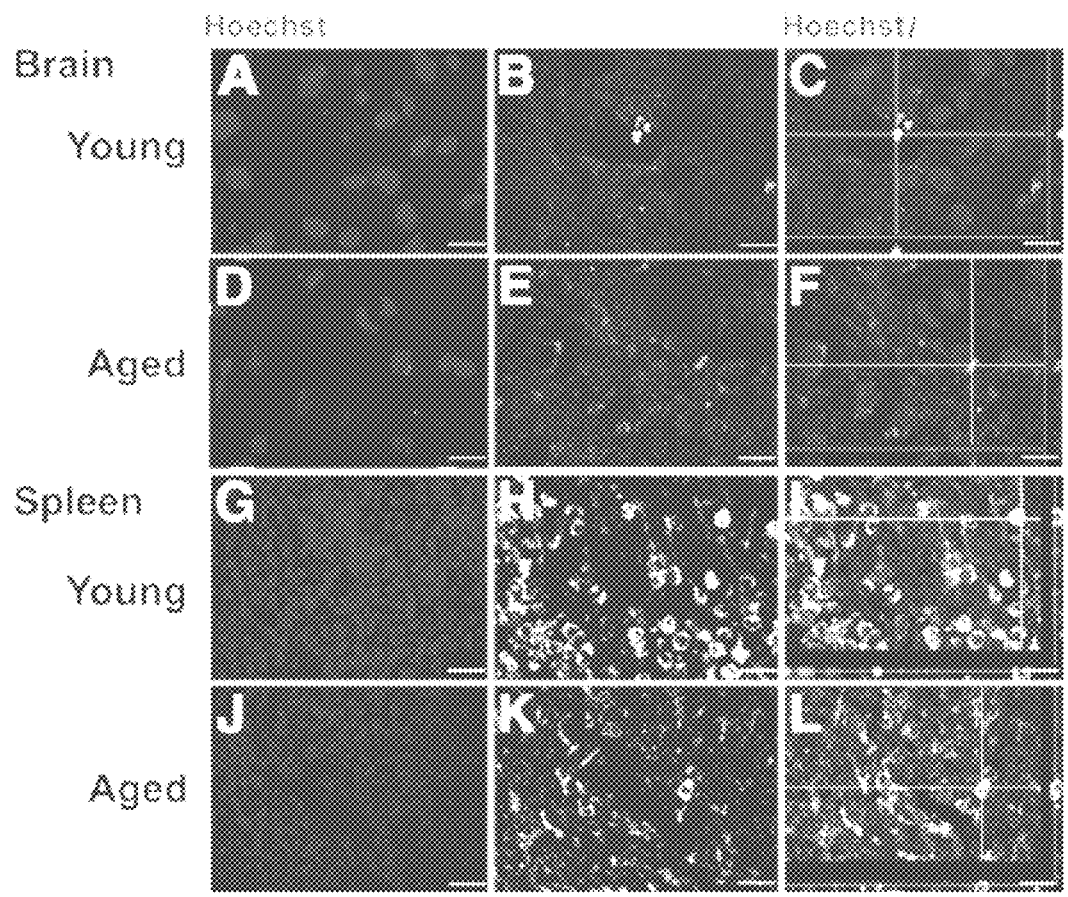
Figure 5A-L

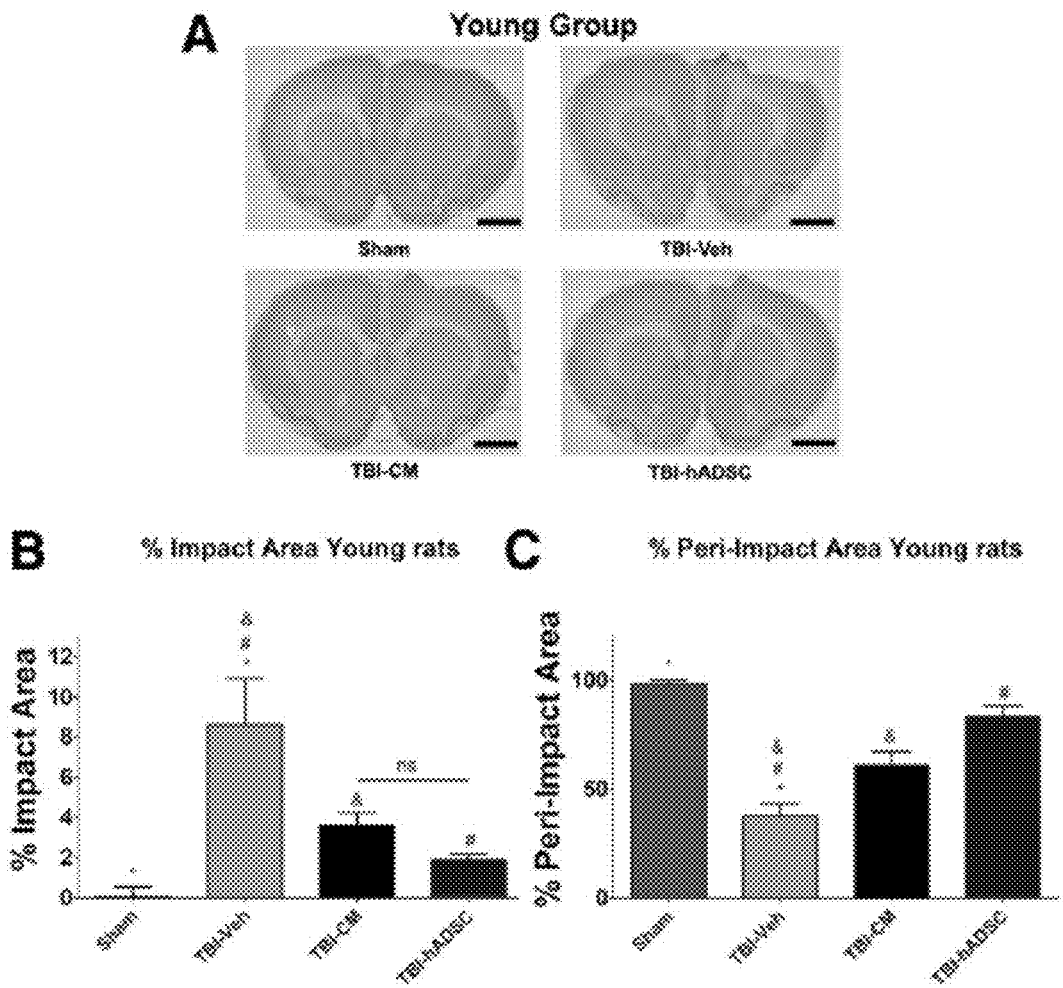
Figure 6A-C

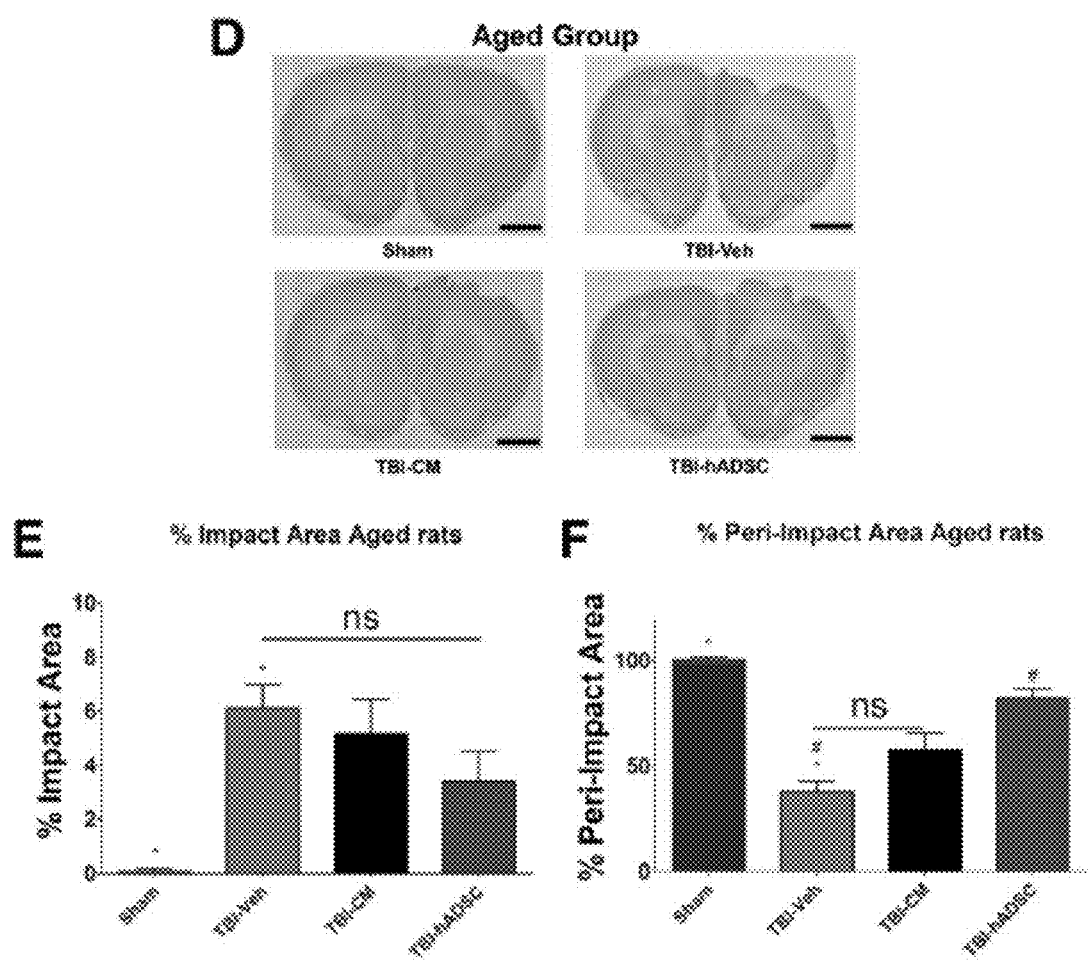
*Figure 6D-F*

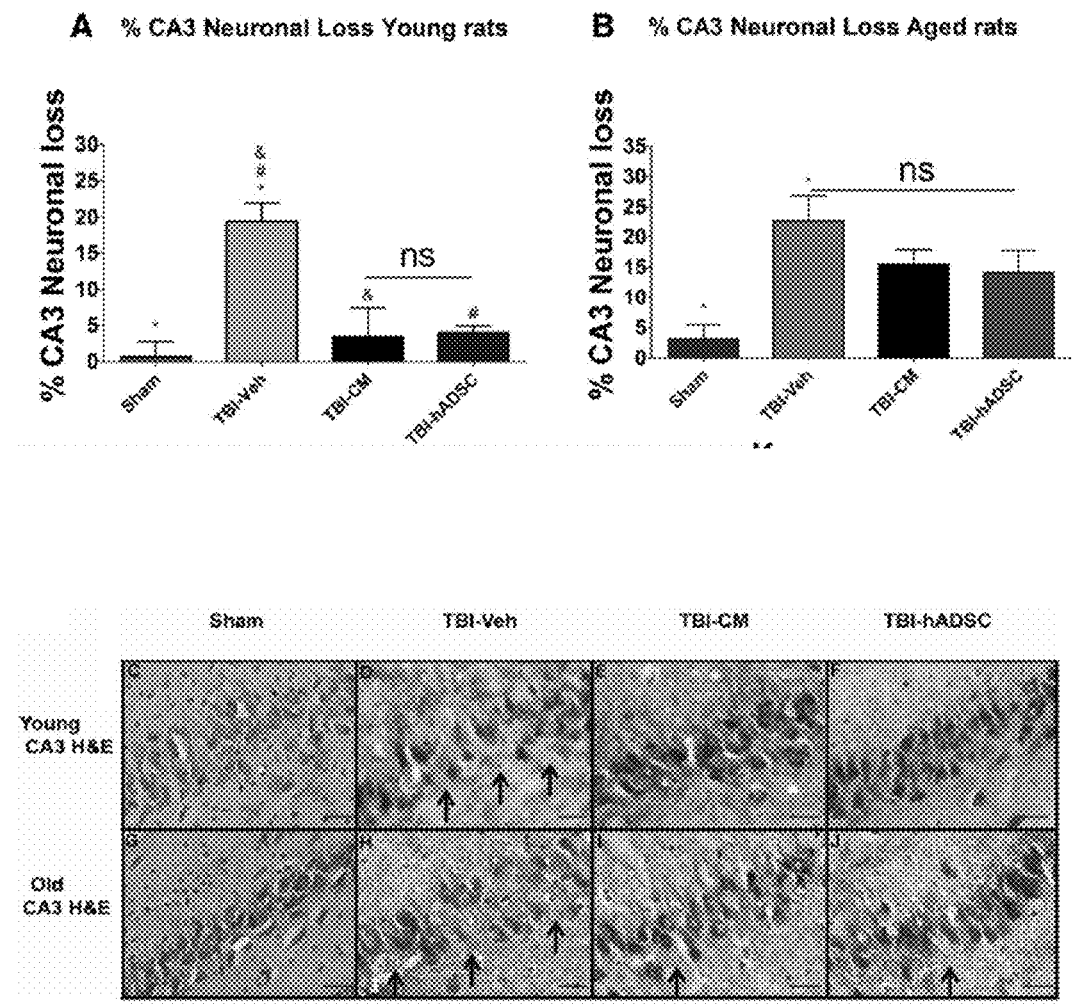
Figure 7A-J

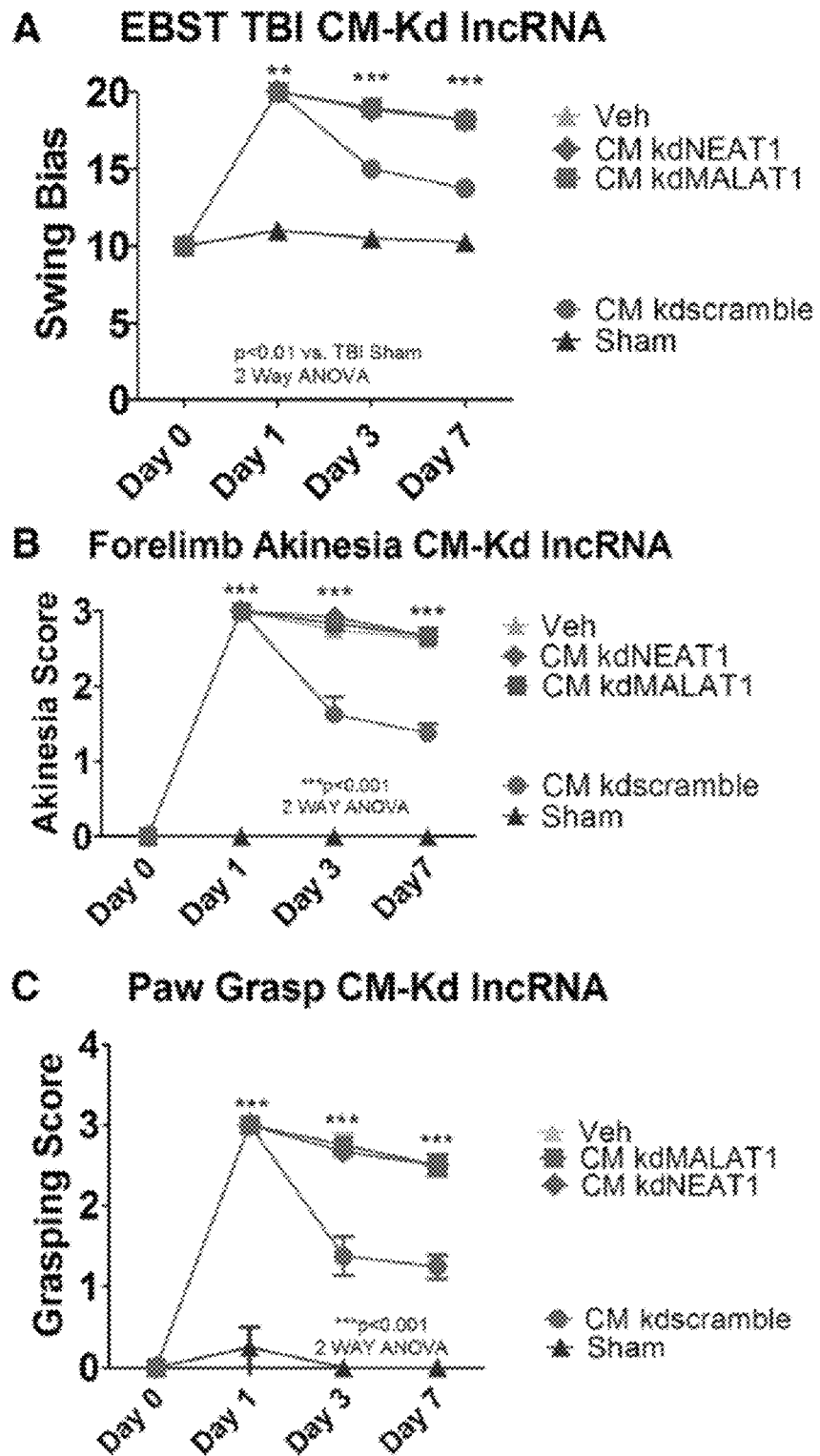
*Figure 8A-C*

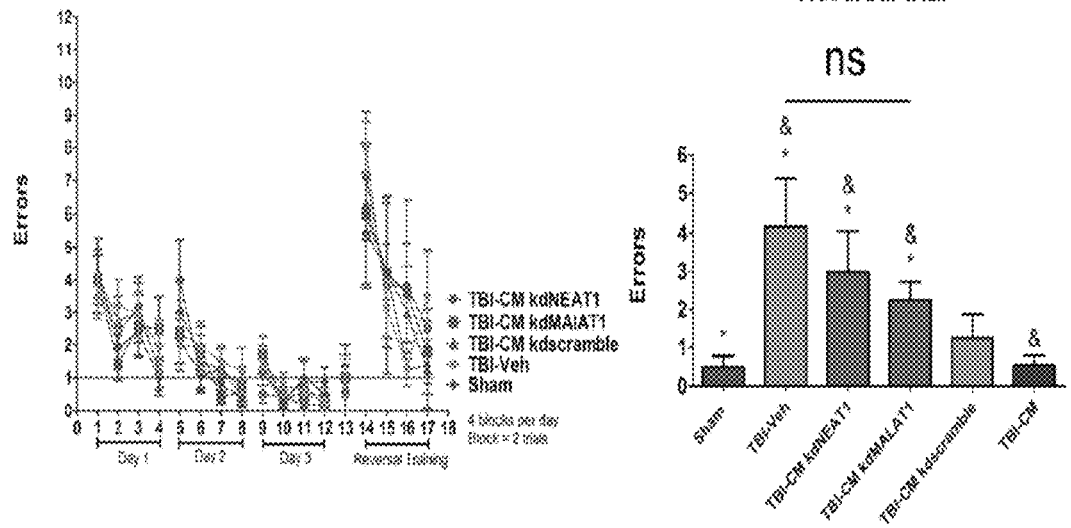
*Figure 9A-B*
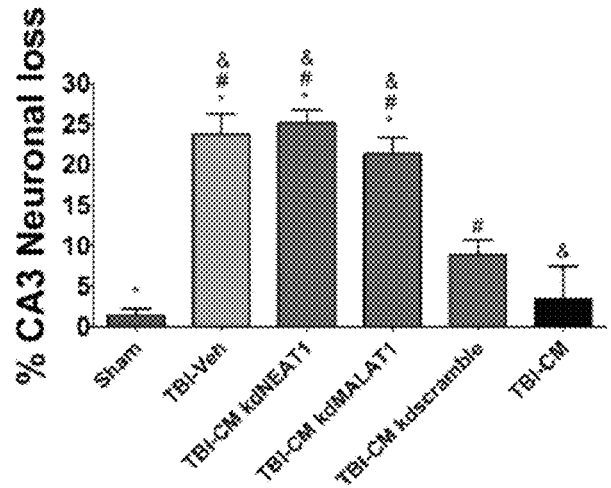
*Figure 10*

METHOD OF TREATING NEUROLOGICAL DISORDERS USING LONG NON-CODING RNAS

CROSS REFERENCE TO RELATED APPLICATIONS

This application is a nonprovisional of and claims priority to U.S. Provisional Patent Application No. 61/930,353, entitled "Method of Treating Traumatic Brain Injury Using Intravenous Transplants of Human Adipose-Derived Stem Cells", filed Jan. 22, 2014, the entire contents of which is herein incorporated into this disclosure.

FIELD OF INVENTION

This invention relates to treating neurological disorders such as traumatic brain injury. Specifically, the invention describes methods of treating traumatic brain injury by administering long non-coding RNAs (lncRNAs) via administration of stem cells expressing the lncRNAs, conditioned media containing lncRNAs or direct administration of lncRNA genes.

BACKGROUND OF THE INVENTION

In the United States, an estimated 2 million Americans both young and aged suffer equally from traumatic brain injury (TBI), which accounts for 30% of all injury-related deaths (Faul M, Xu L, Wanld M M, Coronado V G (2010) Traumatic brain injury in the United States: emergency department visits, hospitalizations, and deaths. Atlanta Ga.: Centers for Disease Control and Prevention, National Center for Injury Prevention and Control). However, aging is considered an independent risk factor for negative health outcomes after TBI. In fact, the incidence of TBI-related morbidities and mortally is higher in the aging population and exponentially increases with age (Hawkins B E, Cowart J C, Parsley M A, Capra B A, Eidson K A, Hellmich H L, Dewitt D S, Prough D S (2013) Effects of trauma, hemorrhage and resuscitation in aged rats. Brain Res 1496:28-35).

Recently, stem cell transplantation has been shown to be an effective regenerative therapy for functional and physiological improvement in animal models of brain disorders such as stroke, Parkinson's disease, Alzheimer's disease, and TBI (Lindvall O, Brundin P, Widner H, Rehncrona S, Gustavii B, Frackowiak R, Leenders K L, Sawle G, Rothwell J C, Marsden C D, Bjorkland A (1990) Grafts of fetal dopamine neurons survive and improve motor function in Parkinson's disease. Science 247:574-577; Clarkson E D (2001) Fetal tissue transplantation for patients with Parkinson's disease: a database of published clinical results. Drugs Aging 18:773-785; Isacson O, Costantini L, Schumacher J M, Cicchetti F, Chung S, Kim K (2001) Cell implantation therapies for Parkinson's disease using neural stem, transgenic or xenogeneic donor cells. Parkinsonism Relat Disord 7:205-212; Bjorklund L M, Sánchez-Pernaute R, Chung S, Andersson T, Chen I Y, Mc-Naught K S, Brownell A L, Jenkins B G, Wahlestedt C, Kim K S, Isacson O (2002) Embryonic stem cells develop into functional dopaminergic neurons after transplantation in a Parkinson rat model. Proc Natl Acad Sci USA 99:2344-2349; Mahmood A, Lu D, Lu M, Chopp M (2003) Treatment of traumatic brain injury in adult rats with intravenous administration of human bone marrow stromal cells. Neurosurgery 53:697-702; discussion 702-703; Yang M, Donaldson A E, Jiang Y, Iacovitti L (2003) Factors influencing the differentiation of dopaminergic traits in transplanted neural stem cells. Cell Mol Neurobiol 23:851-864; Yang M, Donaldson A E, Jiang Y, Iacovitti L (2003) Factors influencing the differentiation of dopaminergic traits in transplanted neural stem cells. Cell Mol Neurobiol 23:851-864; Bjugstad K B, Teng Y D, Redmond D E Jr, Elsworth J D, Roth R H, Cornelius S K, Snyder E Y, Sladek J R (2008) Human neural stem cells migrate along the nigrostriatal pathway in a primate model of Parkinson's disease. Exp Neurol 211:362-369; Muraoka K, Shingo T, Yasuhara T, Kameda M, Yuen W J, Uozumi T, Matsui T, Miyoshi Y, Date I (2008) Comparison of the therapeutic potential of adult and embryonic neural precursor cells in a rat model of Parkinson disease. J Neurosurg 108:149-159; Harting M T, Sloan L E, Jimenez F, Baumgartner J, Cox C S Jr (2009) Subacute neural stem cell therapy for traumatic brain injury. J Surg Res 153: 188-194; Liu Y P, Lang B T, Baskaya M K, Dempsey R J, Vemuganti R (2009) The potential of neural stem cells to repair stroke-induced brain damage. Acta Neuropathol 117:469-480).

An attractive cell therapy for regenerative medicine and wound healing is the use of mesenchymal stem cells (MSCs) derived from adipose tissue and their secretome. Human adipose derived stem cells (hADSCs) have the potential to proliferate, differentiate into different cell lineages, secrete an extensive secretome containing growth factors, cytokines, chemokines, microRNAs, and long noncoding RNA (lncRNA), and have therapeutic potential in TBI (Lendeckel S, Jödicke A, Christophis P, Heidinger K, Wolff J, Fraser J K, Hedrick M H, Berthold L, Howaldt H P (2004) Autologous stem cells (adipose) and fibrin glue used to treat widespread traumatic calvarial defects: case report. J Craniomaxillofac Surg 32:370-373; Xue S, Zhang H T, Zhang P, Luo J, Chen Z Z, Jang X D, Xu R X (2010) Functional endothelial progenitor cells derived from adipose tissue show beneficial effect on cell therapy of traumatic brain injury. Neurosci Lett 473: 186-191).

Of the many lncRNAs that are secreted, two are important for cellular differentiation, nuclear enriched abundant transcript 1 (NEAT1) and metastasis associated lung adenocarcinoma transcript 1 (MALAT1), because of their ability to assist in the alternative splicing of numerous pre-mRNA (Wapinski O, Chang H Y (2011) Long noncoding RNAs and human disease. Trends Cell Biol 21:354-361; Derrien T, Johnson R, Bussotti G, Tanzer A, Djebali S, Tilgner H, Guernec G, Martin D, Merkel A, Knowles D G, Lagarde J, Veeravalli L, Ruan X, Ruan Y, Lassmann T, Carninci P, Brown J B, Lipovich L, Gonzalez J M, Thomas M, Davis C A, Shiekhattar R, Gingeras T R, Hubbard T J, Notredame C, Harrow J, Guigó R (2012) The GENCODE v7 catalog of human long noncoding RNAs: analysis of their gene structure, evolution, and expression. Genome Res 22:1775-1789; Zhang B, Arun G, Mao Y S, Lazar Z, Hung G, Bhattacharjee G, Xiao X, Booth C J, Wu J, Zhang C, Spector D L (2012) The lncRNA Malat1 is dispensable for mouse development but its transcription plays a cis-regulatory role in the adult. Cell Rep 2:111-123). Stem cells, which are in a proliferative, non-differentiating state, secrete numerous lncRNA, including NEAT1 and MALAT1. Stem cells, which are not differentiating, are apparently shedding the factors that would assist in differentiation until appropriate cues are in place.

However, the secretion of lncRNA does not exclude lncRNA uptake by adjacent cells, which could influence survival and regeneration of these cells by undisclosed modalities, including mRNA splicing, migration, and regulation of gene expression (Kim W S, Park B S, Sung J H, Yang J M, Park S B, Kwak S J, Park J S (2007) Wound healing effect of adipose-derived stem cells: a critical role of secretory factors on human dermal fibroblasts. J Dermatol Sci 48:15-24; Ikegame Y, Yamashita K, Hayashi S, Mizuno H, Tawada M, You F, Yamada K, Tanaka Y, Egashira Y, Nakashima S, Yoshimura S, Iwama T (2011) Comparison of mesenchymal stem cells from adipose tissue and bone marrow for ischemic stroke therapy. Cytotherapy 13:675-685; Sun J, Zhou H, Deng Y, Zhang Y, Gu P, Ge S, Fan X (2012) Conditioned medium from bone marrow mesenchymal stem cells transiently retards osteoblast differentiation by downregulating runx2. Cells Tissues Organs 196:510-522).

The majority of cell transplantation studies are performed in young animals. In fact, the inventors now understand that not only is endogenous neurogenesis affected in aging, a few reports suggest that the transplanted stem cells do not survive as well in the aged host (Conboy I M, Conboy M J, Wagers A J, Girma E R, Weissman I L, Rando T A (2005) Rejuvenation of aged progenitor cells by exposure to a young systemic environment. Nature 433:760-764; Carlson M E, Conboy I M (2007) Loss of stem cell regenerative capacity within aged niches. Aging Cell 6:371-382). However, less well studied is the mechanism of action of stem cells and if there may be alterations in migration of cells to various peripheral organs.

SUMMARY OF INVENTION

The inventors have developed a novel and improved method of treating traumatic brain injury (TBI). Traumatic brain injury (TBI) survivors exhibit motor and cognitive symptoms from the primary injury that can become aggravated over time because of secondary cell death.

The inventors evaluated the effects of intravenous administration of hADSCs on motor and cognitive function and their homing pattern during acute and sub-acute periods in young and aged TBI rats with particular emphasis on the spleen, which has been implicated as a major source of systemic inflammation and is known to be necessary for the neuroprotective action of MSCs after TBI pathology (Vendrame M, Gemma C, Pennypacker K R, Bickford P C, Davis Sanberg C, Sanberg P R, Willing A E (2006) Cord blood rescues stroke-induced changes in splenocyte phenotype and function. Exp Neurol 199:191-200; Walker P A, Shah S K, Harting M T, Cox C S Jr (2009) Progenitor cell therapies for traumatic brain injury: barriers and opportunities in translation. Dis Model Mech 2:23-38; Walker P A, Shah S K, Jimenez F, Gerber M H, Xue H, Cutrone R, Hamilton J A, Mays R W, Deans R, Pati S, Dash P K, Cox C S Jr (2010) Intravenous multipotent adult progenitor cell therapy for traumatic brain injury: preserving the blood brain barrier via an interaction with splenocytes. Exp Neurol 225:341-352).

The inventors examined the beneficial effects of human adipose-derived stem cells (hADSCs) in a controlled cortical impact model of mild TBI using young (6 months) and aged (20 months) F344 rats. Animals were transplanted intravenously with $4\times10^6$ hADSCs (Tx), conditioned media (CM), or vehicle (unconditioned media) at least 3 h after TBI. A separate cohort of animals with the same treatments received DiR-labeled hADSCs. hADSCs labeled with DiR were imaged using the IVIS imager at 1, 4, 12, 24, 48 and 72 hours post-transplant, with organs separately imaged at the end of the study. At day 7, post TBI, all groups underwent motor and cognitive assessment tests, then at day 11, all groups were euthanized and brain tissues harvested.

Significant amelioration of motor and cognitive functions was revealed in young, but not aged, Tx and CM groups. Fluorescent imaging in vivo and ex vivo revealed 1,1'-dioactadecyl-3-3-3',3'-tetramethylindotricarbocyanine iodide-labeled hADSCs in peripheral organs and brain after TBI, specifically it was found that hADSCs moved to organs and brain within 1 to 12 hours following TBI. In aged rats, decreased fluorescence was seen in the spleen, however higher fluorescence was observed in the brain at 12-72 hours post TBI. Spatiotemporal deposition of hADSCs differed between young and aged rats, most notably reduced migration to the aged spleen.

Significant reduction in cortical damage and hippocampal cell loss was observed in both Tx and CM groups in young rats, however less neuroprotection was detected in the aged rats. In aged rats, this effect was decreased only in the Tx group but not the CM group. Furthermore, the percentage of intact peri-impact area in the cortex revealed a significant amelioration in both young Tx and CM treated and old Tx and CM rats in comparison with control M. In addition, there was a decrease of hippocampal CA3 pyramidal neuron loss in both young and old Tx rats compared to control M.

To elucidate the hADSC mechanism of action, the inventors examined conditioned media (CM) from hADSCs grown with antisense RNA to silence two lncRNAs (NEAT1 and MALAT1) known to play roles in cell survival, inflammation, and gene expression. CM harvested from hADSCs with silencing of either NEAT1 (nuclear enriched abundant transcript 1) or MALAT1 (metastasis associated lung adenocarcinoma transcript 1), long noncoding RNAs (lncRNAs) known to play a role in gene expression, lost the efficacy in the model.

Results show that hADSCs are a promising therapeutic intervention to rescue against TBI-induced behavioral and histological impairments with better functional recovery in young animals, likely due to robust migration of the transplanted cells to peripheral organs quickly in young animals despite increased stem cell recruitment to the aged ischemic brain. Altogether, hADSCs are promising therapeutic cells for TBI, and lncRNAs in the secretome is an important mechanism of cell therapy. Furthermore, hADSCs showed reduced efficacy in aged rats, which may in part result from decreased homing of the cells to the spleen.

In one embodiment, long-non-coding RNAs are used for treatment of traumatic brain injury and related disorders such as stroke, ischemia, as well as neurodegenerative diseases such as Huntington's disease, Alzheimer's disease and Parkinson's disease. The treatment comprises delivery of either long-non-coding RNAs via stem cells, conditioned media containing long-non-coding RNAs harvested from stem cells, or direct delivery of these long-non-coding RNAs as genes to the area of the nervous system affected. Direct delivery may occur intravenously in some instances or delivery directly into a target tissue such as the area of brain injury in other instances. As an example of long-non-coding RNAs, the invention discloses NEAT1 and MALAT1, but other long-non-coding RNAs secreted by stem cells with similar therapeutic potential, are embodied in this treatment, including, but not limited to, UCHL1, MLL, REST. TUG1, XIST, HOTAIR and MEG3 as well as other lncRNAs that are determined to be efficacious.

A method of improving cognition and inducing and/or enhancing neuroprotection are also presented in alternate embodiments which comprises administration of either long-non-coding RNAs via stem cells, conditioned media containing long-non-coding RNAs harvested from stem cells, or direct delivery of these long-non-coding RNAs as genes to the area of the nervous system affected. Similarly to the method of treatment presented herein, the methods of improving cognition and inducing/enhancing neuroprotection in a patient having a neurological disorder, exemplary lncRNAs that may be administered include, but are not limited to, UCHL1, MLL, REST. TUG1, XIST, HOTAIR and MEG3 as well as other lncRNAs that are determined to be efficacious.

As an example of stem cells, the invention discloses the use of adipose-derived stem cells, but other stem cells, such as mesenchymal stem cells that secrete NEAT1 and MALAT1 as well as similar therapeutic long-non-coding RNAs, may be a source for use in treatment. Examples of stem cells that may be used include, but are not limited to, bone marrow derived stem cells, mesenchymal stem cells, neural progenitor cells, umbilical cord stem cells, and hematopoietic stem cells.

In addition to the disclosed use of long-non-coding RNAs for treatment of TBI and related disorders, another embodiment employs the use of these long-non-coding RNAs as biomarkers for TBI and related disorders. In use as a biomarker, levels of the lncRNAs may be used to diagnose a neurological disorder as defined herein. As an example, a level of expression of NEAT1 or MALAT1 may be taken from a sample from a patient by contacting a sample with an antibody that recognizes NEAT1 or MALAT1 in an immunoassay thereby forming a complex between the lncRNA and the antibody, detecting the complex, comparing the expression level of the complex to a control that represents the level of the lncRNA in normal tissue, and informing the patient as having a neurological disorder if the expression level of the complex is lower than the expression level of the control or informing the patient as to not having a neurological disorder if the expression level of the complex is higher than or equal to the control expression level. If the patient is determined to have a neurological disorder, treatment may be administered as described herein. Further, expression levels may be compared over time to determine efficacy of treatment or progression of disease and favorable or unfavorable outcomes. The antibody used is preferably a monoclonal antibody, however polyclonal antibodies may also be used. The type of immunoassay used is readily determined by those of ordinary skill in the art and includes any immunoassay that may be used to detect a complex between and antibody and an lncRNA.

BRIEF DESCRIPTION OF THE DRAWINGS

For a fuller understanding of the invention, reference should be made to the following detailed description, taken in connection with the accompanying drawings, in which:

FIG. 1 is a flow chart detailing the experimental design. Experiment #1, motor behavioral testing, EBST, forelimb akinesia, and paw-grasp test were performed in young and aged rats before TBI. Young and aged rats were subjected to mild TBI and received transplants of hADSCs, CM, or vehicle 3 h after TBI. After motor and cognitive behavioral evaluations, at days 1, 3, and 7, all rats were killed for immunohistochemical evaluations. Experiment #2, Young and aged rats received transplants of DiR fluorescent labeled hADSCs, CM, or vehicle at 3 h after TBI. IVIS fluorescent imaging was done at 1, 4, 12, 24, and 72 h and day 11 after transplantation. Experiment #3, hADSCs were pretreated with antisense for NEAT1 or MALAT1 or scramble. CM from these cells was collected and infused 3 h after TBI. Motor and cognitive behavioral tests were performed as in Experiment 1. After 11 d after CM infusion, all rats were killed for histological evaluations.

FIG. 2 (A-G) is a series of graphs depicting motor assessment. Results indicate that transplantation of hADSCs or infusion of CM rescued the TBI associated motor deficits in young rats only. Asterisks denote significant difference in motor impairments in young rats transplanted with hADSCs or infused with CM relative to TBI-vehicle group and sham controls in EBST (A), forelimb akinesia (B), and paw-grasp test (C). Two-way ANOVA revealed significant treatment effects as follows: EBST, $F(3,12)=24.66$, $p<0.0001$; Bonferroni's test, ***$p<0.001$; forelimb akinesia, $F(3,12)=16.55$, $p<0.0001$; Bonferroni's test; *$p<0.05$; paw-grasp test, $F(3,12)=31.80$, $p<0.0001$; Bonferroni's test, **$p<0.01$. (D-F) show that there is no significant treatment effects on the motor behavior in aged rats (Bonferroni's test, $p>0.05$). (G) shows a significant correlation between peri-infarct area and EBST motor performance. Data shown are for the young and aged analyzed separately, but the significance remains when the groups are combined ($R^2$ for young=0.93; aged=0.81; combined=0.83; Pearson's r for young=−0.97; aged=−0.91; combined=−0.91).

FIG. 3 (A-D) is a series of graphs depicting Cognitive assessment. Results indicate that cognitive deficits associated with TBI were ameliorated after transplantation of hADSCs in both young and aged rats in reversal training relative to vehicle and sham control. One-way ANOVA revealed significant treatment effects in the young ($F(3,28)=3.95$, $p<0.0185$; Bonferroni's test, $p<0.05$) and aged ($F(3,28)=3.149$, $p<0.01$; Bonferroni's test, *$p<0.05$) rats. CM treatment decrease the cognitive-associated TBI impairments only in young rats relative to vehicle and sham controls ($p<0.05$). A and C shows escape errors (mean±SEM) of young and aged rats, respectively, to find the hidden platform in the RAWM for days 1-3 (4 blocks per day; a block is 2 trials) and for reversal testing on day 4 (trials 1-4). B and D show trial 4 from the reversal training for young and aged rats, respectively.

FIG. 4 (A-E) is a series of images depicting the biodistribution of DiR-labeled hADSCs after TBI. In vivo near-infrared IVIS imaging revealed that the biodistribution and homing of hADSCs is age dependent. A and B show that hADSCs migrated robustly to the spleen and the liver area of young rats exposed to TBI relative to sham controls and to the spleen and liver area of aged rats exposed to TBI and transplanted with hADSCs (one-way ANOVA, $F(3,9)=6.7$, $p<0.001$; Bonferroni's test, ***$p<0.001$). C shows that the migration signal is significantly higher in aged rats only within the first 48 h compared with young and sham control (one-way ANOVA, $F(3,9)=5.61$, $p<0.05$; Bonferroni's test, *$p<0.05$). The migration signal of the labeled hADSCs to the brain of young rats exposed to TBI was low and reached a plateau at 12 h after transplantation compared with aged rats and sham controls. D shows ex vivo near-infrared IVIS imaging of the brain, spleen, lungs, and liver 11 d after TBI. E, Ex vivo fluorescent analysis revealed that spleen and lungs of young rats exposed to TBI expressed higher migration of hADSCs compared with the spleen and lungs of rats exposed to TBI or sham controls; two-way ANOVA, $F(3,9)=14.15$, $p<0.001$; Bonferroni's test, *$p<0.05$). Radiant Efficiency, photons per second per square centimeter per steridian divided by microwatts per square centimeter $$\left(\frac{p/s/cm^2/sr}{\mu W/cm^2}\right)$$

FIG. 5 (A-L) is a series of images depicting Confocal imaging of hADSC-positive expression in the brain and spleen of young and aged rats. Brain confocal images of positive HuNu (green) and Hoechst (blue) and expression of hADSCs (green) within the area of injury in the cortex of young (A-C) and aged (D-F) rats 11 d after transplantation. C and F show a confocal image of a Z-stack reconstruction of HuNu-positive cells colocalizing with Hoechst in young and aged rats, respectively. Spleen confocal images of HuNu- and Hoechst-positive expression of hADSCs in the spleen of young (G-I) and aged (J-L) rats 11 d after transplantation. I and L show confocal Z-stack reconstruction of hADSCs colocalizing with Hoechst in young and aged rats, respectively. I shows a robust migration of hADSCs in the spleen of young relative to the HuNu expression in the spleen of aged rats. Scale bars, 50 μm.

FIG. 6 (A-F) is a series of images depicting hADSC transplantation reduces impact and peri-impact area of young rats exposed to TBI. Nissl staining revealed that hADSC treatment significantly reduced the cortical damage at the impact and peri-impact area associated with TBI injury in young rats. A, Photomicrographs of brain coronal sections of sham-, vehicle-, CM-, or hADSC-treated young rats. B, There is a 50 and 80% reduction of impacted area after treatment with CM and hADSCs, respectively. C, Graphs show that the intact peri-impact area increased 40 and 75% after treatment of CM and hADSCs, respectively (one-way ANOVA, impact area, $F(3,28)=10.54$, $p<0.001$; peri-impact, $F(3,28)=22.98$, $p<0.001$; A-C). Impact and peri-impact analysis of aged rats revealed that treatment of hADSCs partially rescued the TBI-associated cortical damage only in the peri-impact area compared with vehicle and sham controls (D-F). D, Photomicrographs of brain coronal sections of sham-, vehicle-, CM-, or hADSC-treated aged rats. E, Graph shows no significant differences among different treatment in the impact area of aged rats. F, Graph shows that only hADSC treatment increased intact peri-impact area after TBI (ANOVA, peri-impact area, $F(3,28)=30.60$, $p<0.0001$). Scale bars, 1 mm. *, significantly different from sham control; &, significantly different from TBI-CM; #, significantly different from TBI-hADSC; ns, not significant using Bonferroni's test.

FIG. 8 (A-C) is a series of images depicting Knockdowns of NEAT1 and MALAT1 block the CM-mediated motor behavioral improvements in young rats exposed to TBI. Results indicate that treatment of CM kdNEAT1 or CM kdMALAT1 reduced the therapeutic effects seen previously with the treatment of CM when compared with sham control (two-way ANOVA, EBST, $F(3,26)=61.34$, $p<0.0001$; Bonferroni's test, $p<0.01$, *$p<0.001$; forelimb akinesia, $F(3,26)=58.92$, $p<0.001$; Bonferroni's test, *$p<0.001$; pawgrasp, $F(3,26)=36.92$, $p<0.0001$; Bonferroni's test, *$p<0.001$). A, EBST revealed significant asymmetry in days 1, 3, and 7 after TBI in rats treated with either kdNEAT1 or kdMALAT1 relative to CM, CMkdscramble, and sham control. B and C also demonstrate a decrease in forelimb akinesia and paw grasp improvements in days 1, 3, and 7 by blocking either NEAT1 or MALAT1.

FIG. 9 (A-B) is a series of images depicting Knockdown of NEAT1 and MALAT1 blocks the hADSC- and CM-mediated amelioration of cognitive impairments in young TBI rats. Results demonstrated that administration of CM kdNEAT1 or CM kdMALAT1 significantly abrogated the therapeutic benefits seen previously as hADSCs or CM treatment ameliorated the TBI-related memory impairments in the spatial navigation task (one-way ANOVA, $F(3,26)=4.129$, $p<0.01$). There was no amelioration of cognitive function in young rats treated with CM kdNEAT1 and CM kdMALAT1 relative to CM, CM kdscramble, and sham control ($p>0.05$). A shows escape errors (mean±SEM) to find the hidden platform in the RAWM for days 1-3 (4 blocks per day; a block is 2 trials) and for reversal testing on day 4 (trials 1-4) for young rats. B shows trial 4 from the reversal training. *, Significantly different from sham control; &, significantly different from TBI-CM; ns, not significant using Bonferroni's test.

FIG. 10 is a series of images depicting knockdown of NEAT1 and MALAT1 blocks the hADSC- and CM-mediated reduction in hippocampal cell loss in young rats exposed to TBI. Administration of CM kdNEAT1 and CM kdMALAT1 significantly blocked the therapeutic effects relative to CM, CM kdscramble, and sham control (one-way ANOVA, $F(5,31)=23.24$, $p<0.001$). Graph shows the percentage loss of CA3 hippocampal neurons. There is no therapeutic effects to reduce the TBI-associated neuronal cell loss in young rats treated with CM kdNEAT1 or CM kdMALAT1 compared with vehicle, CM, CM kdscramble, or sham control ($p>0.05$). *, Significantly different from sham control; &, significantly different from TBI-CM; #, significantly different from TBI-CM kdscramble using Bonferroni's test.

DETAILED DESCRIPTION OF THE PREFERRED EMBODIMENT

Figure 7K:
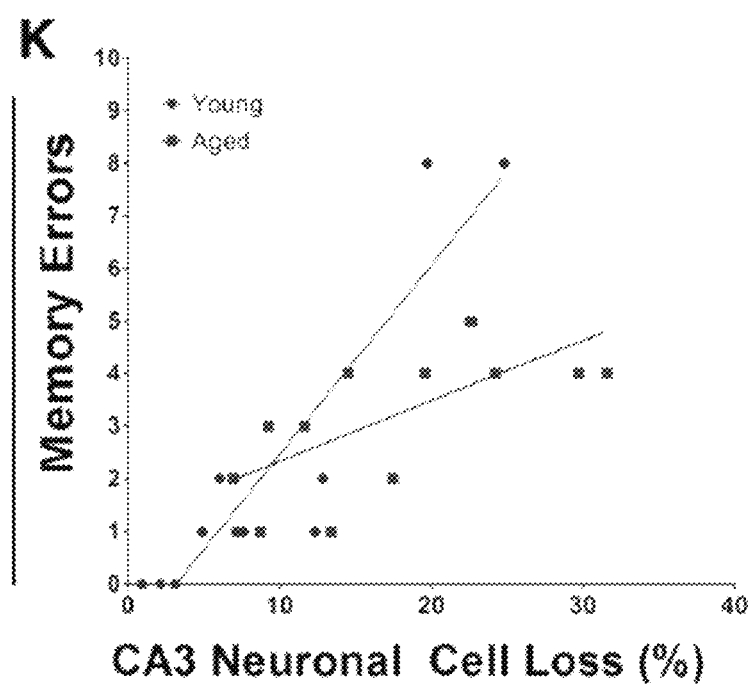
FIG. 7 (A-K) is a hADSC treatment reduces hippocampal cell loss in young TBI rats. Results show that hADSC or CM treatments are neuroprotective in the hippocampus of young rats exposed to TBI and not in aged rats. A shows that there is a significant reduction of the percentage of CA3 neuronal cell loss after treatment with CM or hADSCs compared with vehicle-treated young TBI rats or sham controls (one-way ANOVA, $F(3,28)=7.8$, $p<0.001$). B, Quantitative analyses failed to reveal a significant reduction on the percentage of CA3 neuronal cell loss of aged TBI rats after treatment with hADSC grafts relative to aged vehicle and aged sham control rats ($p>0.05$). C-J, Photomicrographs of H&E staining of ipsilateral dorsal hippocampus, specifically the CA3 region of the hippocampus, in sham, TBI-vehicle, TBI-CM, and TBI-hADSC. Arrows denote neuronal cell loss within the CA3 region. K illustrates the correlation between the number of errors made on trial 4 of the reversal trial (taken from FIG. 3) with the loss of CA3 neuronal cells. There is a significant correlations between memory and CA3 neuronal loss when examined within age groups and between age groups ($R^2$ for young=0.82; aged=0.37; combined=0.60; Pearson's r for young=0.91; aged=0.61; combined 0.78). Scale bars, 50 μm. *, Significantly different from sham control; &, significantly different from TBI-CM; #, significantly different from TBI-hADSC; ns, not significant, using Bonferroni's test.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

"Patient" is used to describe an animal, preferably a human, to whom treatment is administered, including prophylactic treatment with the compositions of the present invention. The terms "patient" and "subject" are used interchangeably herein.

The "therapeutically effective amount" for purposes herein is thus determined by such considerations as are known in the art. A therapeutically effective amount of the adult stem cells, embryonic stem cells, adipose-derived stem cells, long non-coding RNAs, conditioned media from stem cells expressing long non-coding RNAs, bone marrow derived stem cells, neural progenitor cells, umbilical cord stem cells, hematopoietic stem cells, or any combination thereof is that amount necessary to provide a therapeutically effective result in vivo. The amount of adult stem cells, adipose-derived stem cells, long non-coding RNAs, conditioned media from stem cells expressing long non-coding RNAs, or any combination thereof must be effective to achieve a response, including but not limited to total prevention of (e.g., protection against) and to improved survival rate or more rapid recovery, or improvement or elimination of symptoms associated with neurological injury or disorders or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration. In an embodiment in which stem cells are administered to the patient, an exemplary therapeutically effective amount is at least $4 \times 10^6$ viable cells. In an embodiment in which conditioned media containing lncRNAs is administered to the patient, an exemplary therapeutically effective amount is about 500 µl.

"Administration" or "administering" is used to describe the process in which adult stem cells, adipose-derived stem cells, long non-coding RNAs, conditioned media from stem cells expressing long non-coding RNAs, or any combination thereof of the present invention are delivered to a patient. The composition may be administered in various ways including transplantation (including direct transplantation into an area of the nervous system that is affected), parenteral (referring to intravenous and intraarterial and other appropriate parenteral routes), intratheceal, intraventricular, intracisternal, intranigral, intraperitoneal, intraspinal, epidural, intrasynovial, among others. Each of these conditions may be readily treated using other administration routes of stem cells, adipose-derived stem cells, long non-coding RNAs, conditioned media from stem cells expressing long non-coding RNAs, or any combination thereof to treat a disease or condition. The cell population, as described herein, can be administered by any appropriate route which results in delivery to a desired location in the subject where at least a portion of the cells remain viable. The period of viability of the cells after administration to a subject can be as short as a few hours, e.g., twenty-four hours, to a few days, to as long as several years.

The term "treatment" or "treating" as used herein refers to the ability to ameliorate, suppress, mitigate, or eliminate the clinical symptoms after the onset of a disease/injury state. An effective or successful treatment provides a clinically observable improvement. Treatment in the instant invention can result in the amelioration, suppression, mitigation or elimination of cognitive, motor or histological deficits that occurred as a result of the neurological disorder.

"Stem cells", "precursor cells" and "progenitor cells" are used interchangeably herein to refer to a pluripotent, or lineage-uncommitted, progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types. Both adult and embryonic stem cells are contemplated for use herein. As used herein, the term "multipotential" or "multipotentiality" is meant to refer to the capability of a stem cell to differentiate into more than one type of cell. In some embodiments of the instant invention, stem cells which are in a proliferative, non-differentiating state, are useful. Stem cells useful in the instant invention include, but are not limited to, adipose-derived stem cells, mesenchymal stem cells, bone marrow derived stem cells, neural progenitor cells, umbilical cord stem cells, hematopoietic stem cells as well as any other stem cell types that are capable of secreting lncRNAs such as NEAT1, MALAT1, UCHL1, MLL, REST. TUG1, XIST, HOTAIR, MEG3 or other lncRNAs capable of playing roles in cell survival, inflammation, and gene expression.

"Adipose-derived stem cells" or "adipose tissue-derived cells" or "hADSC" as used herein describes stem cells that are derived from adipose tissue. Specifically, the cells act as precursors to a variety of different cell types including, but not limited to, osteocytes/osteoblasts, adipocytes, chondrocytes, neuronal cells, glial cells and myocytes. Adipose-derived stem cells are a subset population of cells derived from adipose tissue, either white or brown, which can be separated from other components of the adipose tissue using standard culturing procedures. The adipose tissue used is preferably mammalian and more preferably human. The adipose-derived stem cells can be isolated from a mixture of cells using the stem cell surface markers disclosed herein. Adipose-derived stem cells include both undifferentiated and differentiated stem cells.

The term "cell" or "cells" is used synonymously herein and refers to in vitro cultures of mammalian cells grown and maintained as known in the art, as well as biological samples obtained from disease specimens or normal specimens in vivo.

"Neurological disorder" as used herein refers to a disorder which impairs the functioning of the central and peripheral nervous system. In some cases, damage may be to the neuronal cells in the brain. Examples include, but are not limited to, traumatic brain injury (TBI), stroke and ischemia as well as neurodegenerative disorders, including, but not limited to, Alzheimer's disease, Huntington's disease and Parkinson's disease. The neurological disorder may be caused by an external force, as in traumatic brain injury, or by an internal occurrence as in stroke, ischemia, Huntington's disease, Alzheimer's disease and Parkinson's disease.

"Traumatic brain injury" or TBI" as used herein refers to an injury to the brain that is caused by an external force. It may result in temporary or permanent neurological damage. Primary brain damage is that damage that occurs at the time of impact, such as bleeding, blood clots, etc., while secondary brain damage is that damage which evolves over time after the impact, such as increased pressure in the skull, brain swelling, seizures, memory loss, etc.

"Stroke" as used herein refers to a condition of the central nervous system in which blood flow to a region of the brain is obstructed which may result in the death of brain tissue. Ischemic stroke is caused by a blockage in a blood vessel that supplies blood to the brain thus resulting in decreased blood flow to the brain. Hemorrhagic stroke is caused by at least one ruptured blood vessel in the brain.

"Long non-coding RNAs" or "lncRNAs" as used herein refers to transcribed RNA molecules having a length of greater than 200 nucleotides that do not encode proteins, mRNA, rRNA, or tRNA. lncRNAs that may be used in the instant invention include, but are not limited to, nuclear enriched abundant transcript 1 (NEAT1) and metastasis associated lung adenocarcinoma transcript 1 (MALAT1) as well as ubiquitin carboxyl-terminal hydrolase isozyme L1 (UCHL1), mixed lineage leukemia or lysine (K)-specific methyltransferase 2A (MLL), RE1 silencing transcription factor. taurine upregulated gene 1 (REST. TUG1), maternally expressed 3 (MEG3), X inactive specific transcript (XIST), Hox transcript antisense RNA (HOTAIR) and combinations thereof. lncRNAs for use in the instant invention include those lncRNAs that play roles in cell survival, inflammation, and gene expression. One of skill in the art may examine the lncRNAs for their efficacy using similar methods as those disclosed herein as used for NEAT1 and MALAT1.

"Conditioned media" as used herein refers to media in which cells have been cultured for a period of time. Specifically, conditioned media is described as media in which stem cells, such as adipose-derived stem cells, have been cultured for at least two passages. The conditioned media of the present invention is enriched with long non-coding RNAs (lncRNAs) from stem cell-secreted exosomes. The conditioned media may also be enriched with other components excreted from the stem cells such as growth factors, trophic factors, chemokines, cytokines, proteins, nucleic acid molecules, etc.

"Improving cognition" as used herein refers to a quantitative increase in cognitive function of the patient.

The term "biomarker" is used herein to refer to a molecule whose level of nucleic acid has a quantitatively differential concentration or level with respect to an aspect of a biological state of a subject. "Biomarker" is used interchangeably with "marker" herein. The level of the biomarker can be measured at the nucleic acid level in which a nucleic acid gene or a transcript which is transcribed from any part of the subject's chromosomal and extrachromosomal genome, including for example the mitochondrial genome, may be measured. Preferably an RNA transcript of an lncRNA, more preferably an RNA transcript includes a primary transcript, a spliced transcript, an alternatively spliced transcript, or an mRNA of the biomarker is measured. A biomarker can be used either solely or in conjunction with one or more other identified biomarkers so as to allow correlation to the biological state of interest as defined herein. Specific examples of biomarkers covered by the present invention include genes involved in cell survival, inflammation, and gene expression. More specifically, biomarkers of the present invention include, but are not limited to, lncRNAs such as nuclear enriched abundant transcript 1 (NEAT1) and metastasis associated lung adenocarcinoma transcript 1 (MALAT1) as well as UCHL1, MLL, REST. TUG1, XIST, HOTAIR and MEG3.

The genes and/or lncRNAs of the present invention may serve as biomarkers for: (1) the diagnosis of disease; (2) the prognosis of diseases (e.g. monitoring disease progression or regression from one biological state to another); (3) the susceptibility or prediction of response to treatment for a disease; or (4) the evaluation of the efficacy to a treatment for disease. For the diagnosis of disease, the level of the specific lncRNA in the subject can be compared to a baseline or control level in which if the level is below the control level, a certain disease is implicated. The prognosis of disease can be assessed by comparing the level of the specific gene biomarker at a first timepoint to the level of the biomarker at a second timepoint which occurs at a given interval after the first timepoint. The prediction of response to treatment for a disease can be determined by obtaining the level of a specific lncRNA biomarker and correlating this level to an overall score. The evaluation of the efficacy of the treatment for a disease can be assessed by comparing the level of the specific biomarker at a first timepoint before administration of the treatment to the level of the biomarker at a second timepoint which occurs at a specified interval after the administration of the treatment.

"Control level" or "baseline level" as used herein refers an expression level of a specific biomarker which is equal to the expression level of the biomarker in normal tissue. This allows a determination based on the baseline level of biomarker expression or biological activity, whether a sample to be evaluated for disease has a measureable increase, decrease, or substantially no change in biomarker expression as compared to the baseline level. In other embodiments, the baseline level can be established from a previous sample from the subject being tested, so that the disease progression or regression of the subject can be monitored over time and/or the efficacy of treatment can be evaluated.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample.

Expression of genes/transcripts represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, Southern blot, Northern blot, sequence analysis, microarray analysis, detection of a reporter gene, or any other DNA/RNA hybridization platforms.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

The terms "diagnosing" or "diagnosis" as used herein refers to the determination of whether a subject comprises a disease or condition such as traumatic brain injury or another neurological disorder.

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

The term "biological state" as used herein refers to the result of the occurrence of a series of biological processes. As the biological processes change relative to each other, the biological state also changes. One measurement of a biological state is the level of activity of biological variables such as biomarkers, parameters, and/or processes at a specified time or under specified experimental or environmental conditions. A biological state can include, for example, the state of an individual cell, a tissue, an organ, and/or a multicellular organism. A biological state can be measured in samples taken from a normal subject or a diseased subject thus measuring the biological state at different time intervals may indicate the progression of a disease in a subject. The biological state may include a state that is indicative of disease (e.g. diagnosis); a state that is indicative of the progression or regression of the disease (e.g. prognosis); a state that is indicative of the susceptibility (risk) of a subject to therapy for the disease; and a state that is indicative of the efficacy of a treatment of the disease.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state, or any portion thereof. Samples can also be from any fluid, tissue or organ including normal and abnormal (diseased) fluid, tissue or organ. Samples from a subject or animal can be used in the present invention as obtained by the subject or animal and processed or cultured such that cells from the sample can be sustained in vitro as a primary or continuous cell culture or cell line.

The term "baseline level" or "control level" of biomarker expression or activity refers to the level against which biomarker expression in the test sample can be compared. In some embodiments, the baseline level can be a normal level, meaning the level in a sample from a normal patient. This allows a determination based on the baseline level of biomarker expression or biological activity, whether a sample to be evaluated for disease cell growth has a measureable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal. In other embodiments, the baseline level can be indicative of a positive diagnosis of disease (e.g. positive control). The term "positive control" as used herein refers to a level of biomarker expression or biological activity established in a sample from a subject, from another individual, or from a population of individuals, where the sample was believed, based on data from that sample, to have the disease. In other embodiments, the baseline level can be established from a previous sample from the subject being tested, so that the disease progression or regression of the subject can be monitored over time and/or the efficacy of treatment can be evaluated.

The term "agent" as used herein describes a composition, compound, chemical or extract that can be administered or tested by the present invention as a modulator of a senescence associated gene. The chemical can be of any composition such as inorganic, organic, or a biomolecule. A biomolecule can be a molecule of any biological origin that can be found in or produced by, at least in part, a cell. This definition includes, but is not limited to, polypeptides, lipids, nucleic acids, carbohydrates and combinations thereof "Agent" is used interchangeably herein with "compound", "composition", "chemical", "drug", and "extract".

The term "gene expression product" or "expression product" as used herein refers to an RNA transcribed from a gene (either pre- or post-processing). An agent is said to increase gene expression if the application of a therapeutically effective amount of the agent to a cell or subject results in an increase in an RNA expression product. An agent is said to decrease gene expression if the application of a therapeutically effective amount of the agent to a cell or subject results in a decrease in an RNA expression product.

The term "polynucleotide" as used herein refers to a polymeric molecule that has a backbone that supports bases capable of hydrogen bonding to typical polynucleotides. The polymer backbone presents the bases in a manner that is effective to allow such hydrogen bonding in a sequence specific fashion between the polymeric molecule and a typical polynucleotide, such as single-stranded DNA. Polymeric molecules include both single and double stranded DNA or RNA and can include polymers having backbone modifications. It includes the recited sequences as well as their complementary sequences, which can be easily ascertained by those of ordinary skill in the art.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized.

The term "differential expression" as used herein refers to qualitative or quantitative differences in the temporal and/or spatial gene expression patterns within and among cells and tissues. A differentially expressed gene may qualitatively have its expression altered, including an activation or inactivation, such as in normal versus diseased tissue. Genes may be turned off or on in a given state relative to another state thus allowing comparison of two or more states. A qualitatively regulated gene may exhibit an expression pattern within a state or cell type that can be detectable by standard techniques. Alternatively, the difference in expression may be quantitative such that expression of the gene is modulated, up-regulated (resulting in an increased amount of transcript), or down-regulated (resulting in a decreased amount of transcript). The degree to which expression varies needs to be large enough to quantify via standard characterization techniques such as expression arrays, quantitative reverse transcriptase PCR, Northern blot analysis, real-time PCR, in situ hybridization, and RNase protection.

The term "expression profile" as used herein refers to a genomic expression profile, for example an expression profile of lncRNAs. The profiles may be generated by any means for determining a level of a nucleic acid sequence, e.g. quantitative hybridization of lncRNA, labeled lncRNA, amplified lncRNA, cDNA, quantitative PCR, ELISA for quantitation, etc. The profile must allow for the analysis of differential gene expression between two samples.

The terms "overexpression" and "underexpression" as used herein refers to the expression of a gene of a patient at a greater or lesser level, respectively, than the normal or control expression of the gene, as measured by gene expression product expression, in a sample that is greater than the standard of error of the assay used to assess the expression. A "significant" expression level may be a level which either meets or is above or below a predetermined score for a gene.

The terms "favorable outcome" or "favorable prognosis" as used herein refers to long time to progression, long term survival, and/or good response. Conversely, an "unfavorable outcome" or "unfavorable prognosis" refers to short time to progression, short term survival, and/or poor response.

The inventors examined the therapeutic potential of hADSC or conditioned media (CM) from hADSC in young and aged rats after TBI, characterized by attenuation of TBI-induced motor, cognitive, and histological deficits, possibly via endogenous repair mechanisms promoted by lncRNA. The inventors demonstrate that hADSC transplantation or CM attenuated the TBI-associated motor and cognitive impairments in young rats but had decreased efficacy in the aged rats.

hADSCs and CM Afford Neuroprotective Effects

Behavioral and histological ameliorations were achieved by hADSC transplantation and CM treatment. The decreased cortical damage and CA3 neuronal loss may directly relate to the motor and cognitive improvement seen in young rats after hADSC treatment. In contrast, hADSC treatment in aged rats only partially rescued the cortical damage, and it has no significant neuroprotective effect in the CA3 region of the hippocampus. Consequently, as seen shown in the Results, there was no improvement of the motor deficits and only partial amelioration on the cognitive function in the aged rats.

Previously, hADSCs have been shown to enhance synaptic plasticity with subsequent reconstruction of the cortical neuronal network (Mizuno H, Tobita M, Uysal A C (2012) Concise review: adipose-derived stem cells as a novel tool for future regenerative medicine. Stem Cells 30:804-810). Certainly, the underlying mechanisms might include functional enhancement of the surviving neurons by either cell to cell interaction or the bystander effect of the CM from the stem cells, which contain a variety of secreted factors, such as chemokines, cytokines, trophic factor, and lncRNA that serve as signaling molecules and anti-inflammatory mediators and might intervene in epigenetic mechanisms for neuroprotection and synaptic plasticity (Egashira Y, Sugitani S, Suzuki Y, Mishiro K, Tsuruma K, Shimazawa M, Yoshimura S, Iwama T, Hara H (2012) The conditioned medium of murine and human adipose-derived stem cells exerts neuroprotective effects against experimental stroke model. Brain Res 1461:87-95; Ribeiro C A, Fraga J S, Grãos M, Neves N M, Reis R L, Gimble J M, Sousa N, Salgado A J (2012) The secretome of stem cells isolated from the adipose tissue and Wharton jelly acts differently on central nervous system derived cell populations. Stem Cell Res Ther 3:18).

Biodistribution of hADSCs

It is now well established that, when cell therapy is administered peripherally as was done in this investigation, the cells migrate to many organs. Migration of cells to the spleen has been implicated as part of the neuroprotective action, as has been shown after both stroke and TBI. The spleen shrinks in the first few days, but this is prevented with stem cell therapy (Vendrame et al., 2006; Walker et al., 2010). Walker et al. (2010) have shown that, after TBI, multipotent adult progenitor cells migrate to the spleen and prevent the shrinkage normally observed after injury.

Early studies demonstrated that intravenous cell therapy has important influences on the monocytes and macrophages in the spleen as an important neuroprotective action in stroke (Vendrame et al., 2006). Additional studies demonstrated that removal of the spleen immediately after TBI or before stroke significantly reduced pro-inflammatory cytokines and improved cognitive function. (Li M, Li F, Luo C, Shan Y, Zhang L, Qian Z, Zhu G, Lin J, Feng H (2011) Immediate splenectomy decreases mortality and improves cognitive function of rats after severe traumatic brain injury. J Trauma 71:141-147; Ajmo C T Jr, Vernon D O, Collier L, Hall A A, Garbuzova-Davis S, Willing A, Pennypacker K R (2008) The spleen contributes to stroke-induced neurodegeneration. J Neurosci Res 86:2227-2234). For this reason, the inventors examined the migration of hADSCs after treatment.

In recent years, several techniques have been applied to track stem cell migration and survival in vivo, including MRI and optical imaging (Solanto M V (1984) Neuropharmacological basis of stimulant drug action in attention deficit disorder with hyperactivity: a review and synthesis. Psychol Bull 95:387-409; Ushiki T, Kizaka-Kondoh S, Ashihara E, Tanaka S, Masuko M, Hirai H, Kimura S, Aizawa Y, Maekawa T, HiraokaM (2010) Noninvasive tracking of donor cell homing by near-infrared fluorescence imaging shortly after bone marrow transplantation. PLoS One 5:e11114; Darkazalli A, Levenson C W (2012) Tracking stem cell migration and survival in brain injury: current approaches and future prospects. Histol Histopathol 27:1255-1261). By using DiR dye, the inventors can easily trace cells in vivo, even through the skull because of its low level of autofluorescence combined with a high wavelength (Michalet X, Pinaud F F, Bentolila L A, Tsay J M, Doose S, Li J J, Sundaresan G, Wu A M, Gambhir S S, Weiss S (2005) Quantum dots for live cells, in vivo imaging, and diagnostics. Science 307:538-544; Boddington S, Henning T D, Sutton E J, Daldrup-Link H E (2008) Labeling stem cells with fluorescent dyes for non-invasive detection with optical imaging. J Vis Exp (14):pii:686; Jang Y Y, Ye Z, Cheng L (2011) Molecular imaging and stem cell research. Mol Imaging 10:111-122; Katsuda T, Tsuchiya R, Kosaka N, Yoshioka Y, Takagaki K, Oki K, Takeshita F, Sakai Y, Kuroda M, Ochiya T (2013) Human adipose tissue-derived mesenchymal stem cells secrete functional neprilysin-bound exosomes. Sci Rep 3:1197; Sugiyama T, Kuroda S, Osanai T, Shichinohe H, Kuge Y, Ito M, Kawabori M, Iwasaki Y (2011) Near-infrared fluorescence labeling allows noninvasive tracking of bone marrow stromal cells transplanted into rat infarct brain. Neurosurgery 68:1036-1047; discussion 1047).

By using in vivo optical imaging, the inventors clearly demonstrate that a small percentage of hADSCs survive and are observed in the injured brain as early as 12 h after injury. The majority of DiR-labeled cells were detected in the spleen/liver region within 1 h after transplantation. A similar pattern of in vivo biodistribution was reported after middle cerebral artery occlusion using 99mTc-hMSC cells into the saphenous vein. (Detante O, Moisan A, Dimastromatteo J, Richard M J, Riou L, Grillon E, Barbier E, Desruet M D, De Fraipont F, Segebarth C, Jaillard A, Hommel M, Ghezzi C, Remy C (2009) Intravenous administration of 99mTc-HMPAO-labeled human mesenchymal stem cells after stroke: in vivo imaging and biodistribution. Cell Transplant 18:1369-1379).

An important observation was that the biodistribution of cells differed in the aged rats after TBI with a higher signal in the aging head, whereas there was a lower signal in the spleen/liver region of aged rats in the subacute stage after TBI and confirmed lower signal in the spleen of aged rats with the ex vivo imaging. The signal observed in the brain was significantly higher at 24 h. One explanation for this is that there is a larger disruption of the blood-brain barrier in the aged versus young rats (Lee P, Kim J, Williams R, Sandhir R, Gregory E, Brooks W M, Berman N E (2012) Effects of aging on blood brain barrier and matrix metalloproteases following controlled cortical impact in mice. Exp Neurol 234:50-61). Despite increased signal at early time points to the aging brain within the subacute stage, these cells failed to fully rescue TBI-mediated motor and cognitive impairment.

There are several potential reasons for the reduced efficacy of the cell therapy in the aged rats. First, as noted, there were fewer HuNu-positive cells observed in the brains of the aged rats, and those HuNu cells that are still present appeared to be dying. This was not observed in the young brain. Thus, one part of the observed difference in efficacy of cell therapy could be related to cell survival in the aged brain and/or spleen. Second, it is possible that the damage is more severe in the aged brain and thus less responsive to therapy. Third, the reduced migration to the spleen may be a critical aspect of the reduced efficacy of the hADSCs in the aged rats. As discussed above, this is thought to be an important aspect of the mechanism of action of cell therapy after brain injury (Walker et al., 2010). The exact reason why hADSCs might show decreased migration to the spleen in the aged rats is not currently established. One explanation is the aged-related decrease in the chemokine profile in aged rats. hADSCs constitutively express chemokine receptors CCR7, CXCRS, and CXCR6 for their corresponding homeostatic chemokines CCL19, CCL21, and CCL20, respectively, which play an important role in cell migration and homing (Baek S J, Kang S K, Ra J C (2011) In vitro migration capacity of human adipose tissue-derived mesenchymal stem cells reflects their expression of receptors for chemokines and growth factors. Exp Mol Med 43:596-603).

Recent studies showed a significantly lower amount of the chemokines CCL19, CCL21, and CCL20 in aged mouse spleen compared with young mice (McDonald K G, Leach M R, Huang C, Wang C, Newberry R D (2011) Aging impacts isolated lymphoid follicle development and function. Immunity Ageing 8:1; Lefebvre J S, Maue A C, Eaton S M, Lanthier P A, Tighe M, Haynes L (2012) The aged microenvironment contributes to the age-related functional defects of CD4 T cells in mice. Aging Cell 11:732-740). Thus, additional studies need to examine whether approaches aimed at increasing these chemokines in the aged spleen could modulate the efficacy of stem cell therapy in the aged. Other approaches could be directed at mechanisms to increase cell survival in the aged animals, because a possible caveat for fewer cells observed in the aged spleen at 11 d after injection is that fewer cells are surviving in the aged spleen, as the inventors suggested may be happening in the aged brain.

Mechanism of CM Efficacy after TBI

One mechanism suggested to play a role in the therapeutic action of hADSCs is that they secrete many important factors. An analysis of the CM used in the experiments described here shows an increase in NEAT1 and MALAT1 and a number of important proteins, such as VEGF and TIMP. It has been shown that hADSC CM enhances neuronal and glial viability and is neuroprotective in stroke (Cho Y J, Song H S, Bhang S, Lee S, Kang B G, Lee J C, An J, Cha C I, Nam D H, Kim B S, Joo K M (2012) Therapeutic effects of human adipose stem cell conditioned medium on stroke. J Neurosci Res 90:1794-1802; Egashira et al., 2012).

It has been shown that hADSCs produce massive secretion of anti-inflammatory cytokines IL-10 and IL-4 in experimental TBI and decrease production of proinflammatory cytokines, such as TNF-$\alpha$ and IFN-$\gamma$, when co-cultured with immune cells, effector T cells, natural killer NK cells, and dendritic cells. (Galindo L T, Filippo T R, Semedo P, Ariza C B, Moreira C M, Camara N O, Porcionatto M A (2011) Mesenchymal stem cell therapy modulates the inflammatory response in experimental traumatic brain injury. Neurol Res Int 2011: 564089; Egashira et al., 2012; Ribeiro et al., 2012; Blaber S P, Webster R A, Hill C J, Breen E J, Kuah D, Vesey G, Herbert B R (2012) Analysis of in vitro secretion profiles from adipose-derived cell populations. J Transl Med 10:172; Singer N G, Caplan A I (2011) Mesenchymal stem cells: mechanisms of inflammation. Annu Rev Pathol 6:457-478)

Because CM showed similar therapeutic potential in young animals, next the inventors examined lncRNAs, which have been postulated previously as regulators of epigenetic mechanisms. hADSC-secreted exosomes carry a complex cargo load of lncRNA (Katsuda et al., 2013), which has been shown previously to improve cardiac function by reducing oxidative stress and inducing the phosphatidylinositol 3-kinase/Akt signaling pathway (Arslan F, Lai R C, Smeets M B, Akeroyd L, Choo A, Aguor E N, Timmers L, van Rijen H V, Doevendans P A, Pasterkamp G, Lim S K, de Kleijn D P (2013) Mesenchymal stem cell-derived exosomes increase ATP levels, decrease oxidative stress and activate PI3K/Akt pathway to enhance myocardial viability and prevent adverse remodeling after myocardial ischemia/reperfusion injury. Stem Cell Res 10:301-312).

There are no published reports on the involvement of lncRNAs in rescuing neurons after brain injury, although over the past decade, there is emerging evidence that lncRNA serves as a key regulator in cell proliferation and survival in mammalian cells (Spadaro P A, Bredy T W (2012) Emerging role of non-coding RNA in neural plasticity, cognitive function, and neuropsychiatric disorders. Front Genet 3:132; Mercer T R, Mattick J S (2013) Structure and function of long noncoding RNAs in epigenetic regulation. Nat Struct Mol Biol 20:300-307).

When expression of NEAT1 or MALAT1 in CM is knocked down with their corresponding antisense RNA in hADSC, CM loses its efficacy to provide neuroprotection and behavioral improvements. It has been shown that NEAT1 and MALAT1 are essential components of nuclear speckles and chromatin, which control stress responses and cellular differentiation (Bond C S, Fox A H (2009) Paraspeckles: nuclear bodies built on long noncoding RNA. J Cell Biol 186:637-644; Clemson C M, Hutchinson J N, Sara S A, Ensminger A W, Fox A H, Chess A, Lawrence J B (2009) An architectural role for a nuclear noncoding RNA: NEAT1 RNA is essential for the structure of paraspeckles. Mol Cell 33: 717-726; Sasaki Y T, Ideue T, Sano M, Mituyama T, Hirose T (2009) MEN epsilon/beta noncoding RNAs are essential for structural integrity of nuclear paraspeckles. Proc Natl Acad Sci USA 106:2525-2530; Naganuma T, Hirose T (2013) Paraspeckle formation during the biogenesis of long non-coding RNAs. RNA Biol 10(8); Nakagawa S, Hirose T (2012) Paraspeckle nuclear bodies-useful uselessness? Cell Mol Life Sci 69:3027-3036).

In addition, MALAT1 significantly influences synapse formation in neuronal culture by controlling the expression of a subset of genes significantly involved in nuclear and synapse function, such as neuroligin 1 and synaptic cell adhesion molecule 1 (Bernard D, Prasanth K V, Tripathi V, Colasse S, Nakamura T, Xuan Z, Zhang M Q, Sedel F, Jourdren L, Coupier F, Triller A, Spector D L, Bessis A (2010) A long nuclear-retained non-coding RNA regulates synaptogenesis by modulating gene expression. EMBO J 29:3082-3093). The inventors postulated that, after TBI, reservoir paraspeckles are released into the cytoplasm, and NEAT1 and MALAT1 play a major role in distributing the pre-mRNA splicing factors to nuclear speckles and thus maintain the regulatory network of brain plasticity. (Fox A H, Lamond A I (2010) Paraspeckles. Cold Spring Harbor Perspect Biol 2:a000687).

In addition to the reduction in NEAT1 or MALAT1, the inventors also examined three biomolecules with potential importance for brain repair. Treatment of hADSCs with antisense to either NEAT1 or MALAT1 partially reduced the presence of both VEGF and SCF and increased the expression of TIMP3, which is an inhibitor of VEGF (Qi J H, Ebrahem Q, Moore N, Murphy G, Claesson-Welsh L, Bond M, Baker A, Anand-Apte B (2003) A novel function for tissue inhibitor of metalloproteinases-3 (TIMP3): inhibition of angiogenesis by blockage of VEGF binding to VEGF receptor-2. Nat Med 9:407-415; Yao J, Jiang S L, Liu W, Liu C, Chen W, Sun L, Liu K Y, Jia Z B, Li R K, Tian H (2012) Tissue inhibitor of matrix metalloproteinase-3 or vascular endothelial growth factor transfection of aged human mesenchymal stem cells enhances cell therapy after myocardial infarction. Rejuvenation Res 15: 495-506). All three of these proteins have been shown to have biological activity in repair after brain injury and thus may also be involved in the protective effect of CM observed in this study. Future studies can address the relative importance of NEAT1 or MALAT1 individually.

Results

To test the hypothesis that administration of hADSC grafts can rescue motor impairments associated with TBI in young and aged rats, a battery of motor behavioral tests, EBST, forelimb akinesia, and paw-grasp tests were conducted.

hADSC Grafts and CM Improve TBI-Associated Motor Asymmetry in Young, but not Aged, TBI Rats EBST revealed that young and old rats subjected to TBI-vehicle exhibited significant asymmetry in motor activity at days 1, 3, and 7 compared with sham control rats (two-way ANOVA, $F_{(3,12)}$=was detected in the young rats treated with either hADSCs or CM compared with young rats subjected to TBI-vehicle and sham controls ($p<0.05$; FIG. 2A). The effect of cell therapy and CM to improve motor asymmetry in young rats exposed to TBI was observed as early as 1 d after treatment and continued throughout the testing period ($p<0.05$; FIG. 2A). Unlike the recovery observed in young rats, aged animals did not display any treatment effect with either hADSC grafts or CM relative to aged rats treated with vehicle and aged sham controls ($p>0.05$; FIG. 2D).

hADSC Grafts and CM Ameliorate TBI Associated Forelimb Akinesia in Young, but not Aged, TBI Rats The forelimb akinesia test demonstrated TBI-associated impairment in forelimb strength in young and aged rats treated with vehicle at all time points compared with sham control rats (two-way ANOVA, $F_{(3,12)}$=12.06, $p<0.001$; FIG. 2B,E). hADSC grafts and CM significantly improved forelimb movement and function in young rats exposed to TBI within the first 24 h, which continued throughout testing period relative to young rats exposed to TBI treated with vehicle and sham controls ($p<0.05$; FIG. 2B). Aged animals subjected to TBI did not display any amelioration of the forelimb akinesia after treatment with either hADSCs or CM relative to aged TBI-vehicle and sham control ($p>0.05$; FIG. 2E). All data are represented as mean±SEM values.

hADSC Grafts and CM Attenuate TBI Associated Paw-Grasp Impairment in Young, but not Aged, TBI Rats Assessment of paw-grasp function demonstrated TBI-associated impairments in paw grasp in both young and aged rats subjected to TBI treated with vehicle at all time points compared with sham control rats (two-way ANOVA, $F_{(3,12)}=31.80$, $p<0.001$; FIG. 2C,F). At 24 h after the onset of TBI, young rats treated with either hADSC grafts or CM scored significantly better on the paw-grasp test compared with young rats exposed to TBI treated with vehicle and sham controls ($p<0.05$; FIG. 2C). There was no significant treatment effect in the paw-grasp assessment of aged rats subjected to TBI treated with hADSCs or CM relative to aged TBI-vehicle and sham controls ($p>0.05$; FIG. 2F). All data are represented as mean±SEM values.

hADSC Grafts and CM Ameliorate TBI Associated Cognitive Impairments Found in RAWM in Young Animals but Showed Reduced Effects in Aged Animals Young and aged sham controls, subjected to TBI treated with vehicle (unconditioned media), hADSC grafts, or CM, were tested for spatial memory using the six-arm spaced training RAWM task to evaluate their cognitive function. In this behavioral paradigm, the rats were trained for four trials a day for 3 consecutive days to find the hidden escape platform.

During the acquisition of learning, there were no differences in performance demonstrating that all groups of rats, young and aged, were able to learn the location of the hidden platform ($p>0.05$; FIG. 3A, C). Of note, there were no disparities of motor function and swimming capabilities, indicating that they were equally able to escape from the water by finding the platform during the allotted 60 s learning trials. hADSC grafts or CM significantly ameliorated the TBI-associated cognitive impairment in young rats relative to young rats treated with vehicle and sham controls (one-way ANOVA, $F_{(3,28)}=22.98$, $p<0.001$; FIG. 3B). There were significant treatment effects on cognitive function in aged rats treated with hADSCs but not with CM relative to aged rats treated with vehicle and sham controls ($p>0.05$; FIG. 3D). All data are represented as mean±SEM values.

Age-Dependent Biodistribution and Homing of Systemically Administered hADSCs In Vivo hADSCs were labeled in vitro with XenoLight and administered through the jugular vein of young and aged rats 3 h after TBI, and their biodistribution was tracked at 1, 4, 12, 24, 48, and 72 h (FIG. 4A-C). Of note, to show that the signal that the inventors detected from the transplanted group was specific for the DiR signal, young and aged sham control rats were subjected to the IVIS imager, and, as expected, there was no fluorescent signal detected. Within the first hour after transplantation, the spleen and liver area of young rats exposed to TBI and transplanted with hADSC-labeled cells expressed a higher fluorescent signal relative to the spleen and liver area of aged rats transplanted with hADSC-labeled cells (one-way ANOVA, $F_{(3,9)}=6.7$, $p<0.001$; FIG. 4B). By 24 h after transplantation, there were no significant differences in fluorescent signaling at the spleen and liver area of either young or aged rats ($p>0.05$; FIG. 4B). The head region analyses revealed that only aged rats exposed to TBI showed a significantly higher signal within the first 24 h compared with young rats subjected to TBI. There was no fluorescent signal detected in the head region of sham controls (ANOVA, $F_{(3,9)}=5.61$, $p<0.05$; FIG. 46). The signal of the labeled hADSCs to the brain of young rats exposed to TBI reached a plateau at 12 h after transplantation compared with aged rats and sham controls.

Age-Dependent Biodistribution and Homing of Systemically Administered hADSCs Ex Vivo At day 11 after transplantation of hADSC, rats were killed, and brain, lungs, liver, and spleen were collected, imaged using the IVIS near-infrared spectrum imager, and processed for immunofluorescence (IF; FIG. 4D,E). Near-infrared IF showed that the biodistribution of hADSCs to organs displayed significant aged-related differences (two-way ANOVA, $F_{(3,9)}=14.15$, $p<0.001$; FIG. 4E). For the near-infrared IVIS imaging, the spleen and lungs of young rats exposed to TBI showed higher fluorescent signals compared with the spleen and lungs of aged rats exposed to TBI or sham controls ($p<0.05$; FIG. 4E). Moreover, the florescence signal detected in the liver of aged rats exposed to TBI was higher relative to young rats subjected to TBI or sham controls ($p<0.05$; FIG. 4E). There was no age related difference in fluorescence signals detected in the brains.

To confirm that the fluorescence signal was related to surviving cells in the animals, the inventors examined immunohistochemistry for HuNu. Less than 1% of the total cells injected were observed at this time after transplantation. Confocal photomicrographs of hADSC expression using IF demonstrated positive expression in brain and spleen from young and aged rats (FIG. 5). HuNu and Hoechst were used to detect the positive hADSCs in the brain and spleen. In the young rats, hADSCs appeared to survive in the brain, although as mentioned, <1% of cells survive to this time after transplantation.

Expression of HuNu-positive cells were found in the ipsilateral cortex within the area as demonstrated by the Z-stack reconstruction of HuNu and Hoechst colocalization. However, in the aged rat, there was a weak HuNu positive expression that can be associated with poor cell survival.

Weak HuNu was found in the ipsilateral cortex within the area of injury. Analysis of the Z-stack reconstruction of the hADSC (HuNu) expression in the spleen of young and aged rats demonstrated a higher migration and survival of hADSCs as depicted by their robust HuNu/Hoechst expression in the young rats relative to aged rats. To further verify that the fluorescent signal observed in the spleen and other organs reflected hADSCs, the inventors examined the spleens of three young rats after injury using flow cytometry.

Although only a very small percentage of the cells in the spleen were DiR positive, 60% of the DiR-positive cells were CD105 positive, and none of the non-DiR cells were CD105 positive (data not shown). As discussed in Materials and Methods, the hADSCs used in this study are 80% CD105 positive at the time of injection; thus, a small percentage of DiR cells have either differentiated or DiR has migrated to other cells.

hADSC Transplantation Reduces Impact and Peri-Impact Area of Young Rats Exposed to TBI Nissl staining revealed that the administered hADSC graft treatment significantly reduced the impact and peri-impact area of TBI injury (one-way ANOVA, impact area, $F_{(3,28)}=10.54$, $p<0.001$; peri-impact, $F_{(3,28)}=22.98$, $p<0.001$; FIG. 6). Quantitative analyses revealed that there is a significant reduction of the damaged impacted area of the cortex of young rats treated with either hADSCs or CM relative to young rats treated with vehicle unconditioned media and sham control ($p<0.05$; FIG. 6B). Of note, there were no significant differences between young rats treated with hADSCs and CM ($p>0.05$; FIG. 6B). Moreover, Nissl analyses revealed a higher percentage of intact peri-impact area on the cortex of young rats exposed to TBI treated with hADSCs and CM relative to young rats treated with vehicle and sham controls ($p<0.05$; FIG. 66).

hADSC Transplantation Partially Ameliorates the Cortical Damage of Aged Rats Subjected to TBI Nissl staining revealed that treatment of hADSCs or CM was not able to reduce the damage of the impacted area of the cortex in aged rats compared with aged rats treated with vehicle media and sham controls ($p>0.05$; FIG. 6E). However, Nissl staining showed that hADSC treatment partially decreased the damage of the cortex in the peri-impact area (ANOVA, $F_{(3,28)}=30.60$, $p<0.001$; FIG. 6F). Quantitative analyses revealed that the percentage of intact peri-impact area of aged rats treated with hADSCs does not differ from aged sham control, and it is significantly greater relative to aged CM and aged vehicle-treated rats ($p<0.0001$; FIG. 6F).

hADSC Grafts and CM Decrease Hippocampal Cell Loss in Young Rats Exposed to TBI but not in the Aged Rats The total number of surviving neurons in the hippocampal CA3 region of young and aged rats exposed to TBI was quantified by H&E staining (FIG. 7). Treatment with hADSCs or CM significantly increases neuronal cells survival in the CA3 region of the hippocampus (one-way ANOVA, $F_{(3,28)}=7.8$, $p<0.001$; FIG. 7). There was a significant decrease on the percentage of neuronal cell loss in the young rats exposed to TBI and treated with either hADSCs or CM compared with young vehicle unconditioned media and sham controls ($p<0.05$; FIG. 7A). Quantitative analyses failed to reveal a significant reduction in CA3 neuronal cell loss in aged rats that received hADSCs or CM treatment grafts ($p>0.05$; FIG. 7B).

Knockdown of NEAT1 and MALAT1 Blocks the CM-Mediated Motor Behavioral Improvements in Young Rats Exposed to TBI To decipher the therapeutic mechanism underlying the observed therapeutic benefits of hADSCs, an additional cohort of young rats was used to test two specific lncRNAs found to be secreted by hADSCs into media. Because knockdown of transcription factors can also alter other biomolecules secreted by the hADSCs into the CM, the inventors also examined three potential bioactive molecules observed in CM. When CM was compared with unconditioned media, the inventors identified 13 proteins that were increased in CM compared with unconditioned media (Table 1); of these, the inventors chose to examine three proteins that have been suggested to have effects on stem cell survival: stem cell factor (SCF), vascular endothelial growth factor (VEGF), and tissue inhibitor of metalloproteinases-3 (TIMP3). As observed in Table 2, knockdown treatment of hADSCs with antisense to NEAT1 or MALAT1 reduces the amount of NEAT1 or MALAT1 in the CM.

TABLE 1

Major proteins secreted into conditioned media

| Factor | Units | UCM | CM | Fold change CM/UCM |
|---|---|---|---|---|
| Adiponectin | ng/ml | >0.29 | 0.58 | >2 |
| B2M | µg/ml | 0.0011 | 0.011 | 10 |
| Compliment C3 | ng/ml | 0.2 | 2.4 | 12 |
| IL-6 | pg/ml | <0.78 | 400 | >100 |
| IL-8 | pg/ml | 1.2 | 12 | 10 |
| MMP-3 | ng/ml | <0.046 | 0.14 | >3 |
| MCP-1 | pg/ml | <9.1 | 191 | >20 |
| PAI-1 | ng/ml | <0.031 | 259 | >100 |
| SCF | pg/ml | <12 | 13 | >1 |
| TIMP-1 | ng/ml | 0.05 | 45 | 900 |
| TNFR2 | ng/ml | 0.006 | 0.013 | 2.2 |
| VCAM-1 | ng/ml | <0.025 | 0.067 | >2 |
| VEGF | pg/ml | 15 | 247 | 16.5 |

MCP-1, Monocyte chemoattractant protein; MMP-3, matrix metalloproteinase-3; PAI-1, plasminogen activator inhibitor-1; TNFR2, TNF receptor-2; UCM, unconditioned medium; VCAM-1, vascular cell adhesion molecule 1.

TABLE 2

Effect of knockdown of NEAT1 or MALAT1 on conditioned media

| Media condition | NEAT1 (% control) | MALAT1 (% control) | VEGF (% control) | SCF (% control) | TIMP3 (% control) |
|---|---|---|---|---|---|
| Control CM | 100 ± 3 | 100 ± 5 | 100 ± 8 | 100 ± 8 | 100 ± 7 |
| Antisense NEAT1 | 15.3 ± 5[1] | 71.5 ± 5 | 27.6 ± 15[1] | 28.4 ± 3[1] | 400 ± 26[1] |
| Antisense MALAT1 | 87.4 ± 4 | 5.5 ± 4[1] | 42.8 ± 24[1] | 63.1 ± 8[1] | 290 ± 32[1] |

[1]$p < 0.01$ versus control CM

In addition, there is also a significant reduction in VEGF and SCF measured in the CM (VEGF, one-way ANOVA, $F_{(3,19)}=482$, $p<0.001$; post hoc tests revealed that CM was different from either kdNEAT1 or kdMALAT1 at $p<0.001$; SCF, $F_{(3,19)}=336.4$, $p<0.001$; post hoc tests revealed the difference between CM and kd-NEAT1 or kdMALAT1 at $p<0.001$). When the inventors examined TIMP3 in the CM, there was an increase in the CM from the cells treated with antisense to NEAT1 or MALAT1 compared with CM (one way ANOVA, $F_{(3,17)}=59.51$, $p<0.0001$; post hoc tests, $p<0.001$ comparing CM with kdNEAT1 or kdMALAT1).

The inventors observed that either CM kdNEAT1 or CM kdMALAT1 reduced the therapeutic effects seem previously with the treatment of CM when compared with sham control (two-way ANOVA, EBST, $F_{(3,26)}=61.34$, $p<0.001$; forelimb akinesia, $F_{(3,26)}=58.92$, $p<0.001$; paw grasp, $F_{(3,26)}=36.92$, $p<0.001$; FIG. 8). EBST demonstrated significant asymmetry in motor activity at days 1, 3, and 7 after TBI (p 0.01) in rats treated with either kdNEAT1 or kdMALAT1 relative to CM, CM kdscramble, and sham control (FIG. 8A). Moreover, blocking either NEAT1 or MALAT1 lowered the efficacy of the CM to improve motor functional performance on forelimb akinesia and the paw-grasp test ($p<0.05$; FIG. 8B, C). These observations suggest that lncRNAs, NEAT1, and MALAT1 play a key role in sustaining long-term neuroprotection and behavioral improvement.

Knockdown of NEAT1 and MALAT1 Blocks the hADSC- and CM-Mediated Amelioration of Cognitive Impairments in Young TBI Rats Young sham controls subjected to TBI treated systemically with CM kdNEAT1, CM kdMALAT1, CM kdscramble, or CM were tested for spatial memory using the six-arm spaced training RAWM task (FIG. 9). As described previously in this study, the rats were trained for four trials a day for 3 consecutive days to find the hidden escape platform. During the acquisition of learning, there were no differences in performance, demonstrating that all groups of rats, young and aged, were able to learn the location of the hidden platform ($p>0.05$; FIG. 9A). Of note, there were no disparities of motor function and swimming capabilities, indicating that they equally escaped from the water by finding the platform during the allotted 60 s learning trials. Administration of CM kdNEAT1 or CM kdMALAT1 significantly abrogated the therapeutic benefits seen previously because hADSCs or CM treatment ameliorated the TBI-related memory impairments in the spatial navigation task (one-way ANOVA, $F_{(3,26)}=4.129$, $p<0.01$; FIG. 9B). All data are represented as mean±SEM values. There was no amelioration of cognitive function in young rats treated with CM kdNEAT1 and CM kdMALAT1 relative to CM, CM kdscramble, and sham control ($p<0.05$).

Knockdown of NEAT1 and MALAT1 Blocks the hADSC- and CM-Mediated Reduction in Hippocampal Cell Loss in Young Rats Exposed to TBI After systemic administration of kd lncRNAs and appropriate controls, the total number of surviving neurons in the hippocampal CA3 region of young rats was quantified by H&E staining (FIG. 10). Administration of CM kdNEAT1 and CM kdMALAT1 significantly blocked the therapeutic effects relative to CM, CM kdscramble, and sham control (one-way ANOVA, $F_{(5,31)}=23.24$, p<0.001; FIG. 10). There was no therapeutic effect to reduce the TBI-associated neuronal cell loss in young rats treated with CM kdNEAT1 and CM kdMALAT1 compared with CM, CM kdscramble, and sham control (p>0.05; FIG. 10).

Materials and Methods

Subjects.

Experimental procedures were approved by the University of South Florida Institutional Animal Care and Use Committee (IACUC). All animals were housed under normal conditions (20° C., 50% relative humidity, and a 12 h light/dark cycle). All studies were performed by personnel blinded to the treatment condition.

Fluorescent Labeling of Cultured hADSC Grafts and CM Preparation.

hADSCs were obtained from ZenBio (catalog #ASC-S). According to the protocol of the manufacturer, cells ($6.7 \times 10^5$ cells/T75 flask) were suspended in 10 ml of supplemented growth medium (PM-1; ZenBio) and grown in non-coated T-75 flasks at 37° C. in humidified atmosphere containing 5% carbon dioxide. hADSCs were grown until they were 90% confluent and then subcultured. Cells were routinely assessed by flow cytometry for stem cell markers and were verified as $CD31^-$, $CD34^-$, $CD45^-$, $CD106^-$, $CD117^-$ and $CD44\ 90\%^+$, $CD73\ 89\%^+$, $CD105\ 80\%^+$, $CD90\ 97\%^+$. Thus, three major markers that are routinely used to define MSCs, CD105, CD73, and CD90, are present and endothelial or hematopoietic markers are absent. This profile remained stable for 10 passages; all cells used in this study for transplantation or generation of CM were between two and nine passages. Cells were also routinely assessed for multipotency using methods as published previously. Differentiation into osteoblasts was performed by culturing cells in osteoblast differentiation medium (DM; ZenBio) for 4 weeks with changes every 5 d. Positive staining for Alizarin Red (1% Alizarin Red; CM-0058; Lifeline Technology) was used to verify osteoblast differentiation. Cells were fixed in PBS-10% Formalin for 20 min, washed once with PBS, stained with 1% Alizaren Red S for 5 min, washed again three times, and visualized in a light microscope. Differentiation to adipocytes was performed using DM2 adipocyteDM (ZenBio) for 12 d with medium changes every 5 d. Oil Red was used to identify adipocytes. Cells were fixed in PBS-10% Formalin for 1 h, washed in isopropanol, and dried. Oil Red 0 working solution was added for 10 min and then washed four times with PBS.

Cells were imaged using a light microscope. hADSCs were able to differentiate into both osteoblasts and adipocytes. For graft preparation, hADSCs were harvested, and the cell density was adjusted as $4 \times 10^6$ cells in 500 µl of PBS. Then cells were incubated with XenoLight 1,1'-dioctadecyl-3,3,3',3'-tetramethylindotricbocyanine iodide (DiR) (catalog #125964; Caliper Life Sciences) for 30 min to evaluate migration of the transplanted hADSCs. After the labeling, cells were rinsed using PBS and centrifuged twice. Thereafter, the pellet of labeled cells was suspended in 500 µl of PBS just before the transplantation. In each passaging, CM was collected from hADSC culture, filtered using 0.45 mm pore sized filter to avoid cells contamination, and cryopreserved for additional experiments. For the present study, the inventors used the CM from cells at passages 2 to 4.

Preparation of hADSC-Derived CM with Knockdown of NEAT1 and MALAT1.

The cultured hADSCs at 80% confluence were treated with antisense RNA (NEAT1 and MALAT1 or scramble control obtained from ISIS Pharmaceuticals) that was incorporated into the cells for 48 h, and CM was collected for 24 h and stored at −80° C. until needed. CM was verified to be deficient of either NEAT1 or MALAT1 in the appropriate conditions, and no change in either was observed with the scrambled antisense RNA control.

Measurement of Human Vascular Endothelial Growth Factor, Stem Cell Factor, and Tissue Inhibitor of Metalloproteinase 3 Concentration.

Cell supernatant was measured by Human VEGF Quantikine ELISA Kit (DVE00; R&D Systems), Human SCF Quantikine ELISA Kit (DCKOO; R&D Systems), and Human TIMP-3 DuoSet (DY973; R&D Systems), according to the instructions of the manufacturer. Absorbance from each sample was measured using a Synergy HT plate reader (Bio-Tex) at 450 nm.

Surgical Procedures.

A total of 82 Fisher 344 male rats, young (6 months, n=48) and aged (20 months; n=34), were subjected to either TBI using the controlled cortical impact (CCI) injury model (Pittsburgh Precision Instruments) or sham control (no TBI). The total number of rats in each group was as follows: n=9 for young TBI-hADSC; n=8 for young TBI-CM; n=6 for young TBI-CM knockdown (kd) NEAT1; n=6 for young TBI-CM kdMALAT1; n=4 for young TBI-CM kdscramble; n=7 for young TBI-vehicle; n=8 for young sham control; n=11 for aged TBI-hADSC; n=8 for aged TBI-CM; n=8 for aged TBI-vehicle; and n=7 for aged sham control. Deep anesthesia was achieved using 1-2% isoflurane, and it was maintained using a gas mask. All animals were fixed in a stereotaxic frame (David Kopf Instruments). After exposing the skull, coordinates of +0.2 mm anterior and +0.2 mm lateral to the midline were used and impacted the brain at the frontoparietal cortex with a velocity of 6.0 m/s, reaching a depth of 0.5 mm (mild TBI) below the dura matter layer and remaining in the brain for 150 ms. The impactor rod was angled 15° vertically to maintain a perpendicular position in reference to the tangential plane of the brain curvature at the impact surface. A linear variable displacement transducer (Macrosensors) that was connected to the impactor measured the velocity and duration to verify consistency. Sham control injury surgeries (i.e., uninjured animals) consisted of animals exposed to anesthesia, scalp incision, craniectomy, and suturing. An electric drill was used to performed the craniectomy of ~4 mm radius centered from bregma +0.2 anterior and +0.2 mm lateral right (Paxinos G, Watson C (2007) The rat brain in stereotaxic coordinates, Ed 6. Amsterdam: Academic/Elsevier). A computer-operated thermal blanket pad and a rectal thermometer allowed maintenance of body temperature within normal limits. All animals were closely monitored postoperatively with weight and health surveillance recording as per IACUC guidelines. Rats were kept hydrated at all times, and the analgesic ketoprofen was administered after TBI surgery and as needed thereafter. Before and after TBI, rats were fed regular rodent diet. A schematic diagram of the experimental design is shown (FIG. 1).

Intravenous Administration of hADSCs, CM, and Vehicle.

Three hours after TBI surgery, rats were anesthetized with 1-2% isoflurane in nitrous oxide/oxygen (69%/30%) using a face mask. Vehicle (unconditioned media; 500 µl of sterile media PM-1 that was not incubated with cells), CM (500 µl of CM, CM kdNEAT1, CM kdMALAT1, CM kdscramble), or hADSC grafts (4×10⁶ viable cells in 500 µl of sterile saline) were administered via the jugular vein.

XenoLight DiR for In Vivo and Ex Vivo Biodistribution Imaging Procedures.

Young and aged rats were subjected to TBI using the CCI injury model (Pittsburgh Precision Instruments). DiR-labeled 4×10⁶ hADSCs (Tx group) were then transplanted into the jugular vein at 3 h after TBI. To visualize DiR fluorescence emitted from the engrafted hADSCs in vivo, animals were shaved to avoid light scattering and anesthetized in a chamber with 3.0% isoflurane. Once the rats were completely anesthetized, the animals were transferred from the chamber to the IVIS Spectrum 200 Imaging System (Xenogen), and the isoflurane level was set at 1-2% until complete image acquisition.

The biodistribution of DiR-labeled hADSC grafts was monitored at 1, 4, 12, 24, 48, and 72 h after transplant. Rats were imaged ventrally at all time points. A second set of images were obtained for the head region using a higher magnification. Identical illumination parameters [exposure time=Auto; lamp voltage=high; f/stop=2; field of view=B (for head) and C (for whole body); binning=8; emission filter=800 nm; and excitation filter=745 nm] were selected for each acquisition. All captured images were analyzed with Living Image software 4.0 (Xenogen). To analyze the change in DiR fluorescence intensity, identical regions of interest (ROIs) were placed on the abdomen and head area for animals. The same ROI was also placed on the control animal as the background reference. Background efficiency was subtracted from each of the individual animal's efficiency and presented as an average radiant efficiency (photons per second per square centimeter per steridian divided by microwatts per square centimeter).

Behavioral Testing.

Each rat was subjected to a series of behavioral tests to reveal motor, neurological, and cognitive performance of animals, before and after TBI and after transplantation. The tests included the elevated swing test (EBST), forelimb akinesia, and paw-grasp test before and after TBI at days 0, 1, 3, and 7. The radial arm water maze (RAWM) test was performed on day 7 after TBI surgery.

EBST Test.

EBST is a measure of asymmetrical motor behavior that does not require animal training or drug injection (Borlongan C V, Sanberg P R (1995) Elevated body swing test: a new behavioral parameter for rats with 6-hydroxydopamine-induced hemiparkinsonism. J Neurosci 15:5372-5378). The rats were held, in the vertical axis, ~1 inch from the base of its tail and then elevated to an inch above the surface on which it has been resting. The frequency and direction of the swing behavior were recorded for 20 tail elevations. A swing was counted when the head of the rat moved >10° from the vertical axis to either side. The total number of swings made to the biased side was added per group and divided by the n, giving us the average number of swings per treatment group.

Forelimb Akinesia Test.

Before and after TBI surgery, young and aged rats from sham control, TBI-vehicle, TBI-hADSC, or TBI-CM were evaluated for forelimb akinesia (Borlongan C V, Hida H, Nishino H (1998) Early assessment of motor dysfunctions aids in successful occlusion of the middle cerebral artery. Neuroreport 9:3615-3621). Ipsilateral and contralateral forepaw strength and motility were scored by two experimentally blinded evaluators using the following forelimb akinesia scale. On a scale of 1 to 3, 1 is normal, 2 is impaired, and 3 is severely impaired. Scores were tallied for each individual animal, and then mean scores for treatment groups were used for analyses.

Paw-Grasp Test.

Before and after TBI surgery, grip strength of young and aged rats from sham control, TBI-vehicle, TBI-hADSC, or TBI-CM were evaluated. An abnormal grip is indicative of impaired neuromuscular function. In this test, rats were held by their bodies against a pole (Ibrahim A G, Raisman G, Li Y (2009) Permanent loss of fore-paw grasping requires complete deprivation of afferent input from a minimum of four dorsal roots of the rat brachial plexus. Exp Neurol 215:142-145). Both ipsilateral and contralateral paw grip strength were scored by two experimentally masked evaluators using the following grip strength scale. In a scale of 1 to 3, 1 is normal, 2 is impaired, and 3 is severely impaired. Scores were tallied for each individual animal, and then mean scores for treatment groups were used for analyses.

RAWM Test.

The RAWM test allows the investigator to analyze basic parameters, such as place or spatial learning. The acquisition of learning is when the animal must learn how to use distal cues to navigate through the arms to find the hidden platform. Also, it has been shown that RAWM spatial learning is not dependent on locomotor ability, because this does not affect swimming speed (Vorhees C V, Williams M T (2006) Morris water maze: procedures for assessing spatial and related forms of learning and memory. Nat Protoc 1:848-858). Each error shows the ability to search and learn to use distal cues to find the platform. To reveal the cognitive effects of hADSC grafts on spatial navigation and memory of young and aged TBI rats, RAWM, a hippocampal-dependent task, was tested. RAWM started on day 7 after TBI surgery and intravenous transplantation of hADSC grafts and CM.

Six-arm RAWM was placed in a water tank of ~150 cm diameter, and a 40-cm-height, 10-cm-diameter platform was used. The platform was submerged 1 cm below the surface of water. The temperature of the water was kept at 27° C. Rats were placed on the start arm at the beginning of every trial, and the platform was located on the goal arm. Every animal had an assigned platform/arm location throughout acquisition of learning, yet the starting zone was randomly changed per trial. A space training protocol was followed. Rats were given two blocks of four trials, with each block separated by 30 min rest period per day, for a total of eight trials a day for 3 d of acquisition of learning. Trials were only 60 s long. Once animals found their goal arm/platform, they were allowed to remain on the platform for 30 s between trials. If rats were unable to find their goal arm/platform within 60 s, rats were guided to their goal arm and allowed to rest on the platform for 30 s. On day 4, a probe trial was given 1 h before reversal training started, placing the rat 180° from the goal arm. Rats were given four trials to train for the new position (reversal training). RAMW performance analysis was done by averaging the trials per block, using four trials per block and then a total of two blocks per day (errors are given every time rats are not entering the goal arm). Reversal training was analyzed by counting the total of errors in each trial.

Brain and Organ Harvesting, Fixation, and Sectioning.

Under deep anesthesia, rats were killed on day 11 after TBI for immunohistochemical investigations. Briefly, animals were perfused through the ascending aorta with 200 ml of cold PBS, followed by 200 ml of 4% paraformaldehyde in phosphate buffer (PB). Brains, spleen, lungs, and liver were removed and postfixed in the same fixative for 24 h, followed by 30% sucrose in PB until completely sunk. Six series of coronal sections were cut at a thickness of 30 μm with a cryostat and stored at −20° C.

Measurement of Impact and Peri-Impact Area: Nissl Staining Analysis.

Serial sections corresponding to the same group of animals were stained with Nissl for impact- and peri-impact calculations. Six coronal sections between the anterior edge and posterior edge of the impacted area were collected and processed for Nissl staining from each brain perfused at day 11 after TBI. Sections were cut at a thickness of 30 μm by a cryostat. Every sixth coronal tissue section, beginning at anteroposterior (AP)+2.28 mm and ending at AP 0 mm posterior from bregma, was randomly selected for measurement of impact- and periimpact area. Brain sections were examined using a light microscope (Olympus) and Keyence microscope. The impact area of brain damage was measured in each slice and quantified by a computer-assisted image analysis system (NIH Image) and calculated by the following formula:

[(area of the damaged region in each section)×0.030] (cubic millimeters)

The peri-impact area of brain damage was counted by a computer assisted image analysis system (NIH Image). Impact and peri-impact area was then expressed as a percentage of the ipsilateral hemisphere compared with the contralateral hemisphere.

Measurement of Hippocampal Cell Loss: Hematoxylin and Eosin Staining Analysis.

Hematoxylin and eosin (H&E) staining was performed to confirm the core impact injury of the TBI model. As shown in the previous studies, the inventors demonstrated primary damage to the frontoparietal cortex. (Hayashi T, Kaneko Y, Yu S, Bae E, Stahl C E, Kawase T, van Loveren H, Sanberg P R, Borlongan C V (2009) Quantitative analyses of matrix metalloproteinase activity after traumatic brain injury in adult rats. Brain Res 1280:172-177; Yu S, Kaneko Y, Bae E, Stahl C E, Wang Y, van Loveren H, Sanberg P R, Borlongan C V (2009) Severity of controlled cortical impact traumatic brain injury in rats and mice dictates degree of behavioral deficits. Brain Res 1287:157-163; Glover L E, Tajiri N, Lau T, Kaneko Y, van Loveren H, Borlongan C V (2012) Immediate, but not delayed, microsurgical skull reconstruction exacerbates brain damage in experimental traumatic brain injury model. PLoS One 7:e33646; Acosta S A, Tajiri N, Shinozuka K, Ishikawa H, Grimmig B, Diamond D, Sanberg P R, Bickford P C, Kaneko Y, Borlongan C V (2013) Long-term upregulation of inflammation and suppression of cell proliferation in the brain of adult rats exposed to traumatic brain injury using the controlled cortical impact model. PLoS One 8:e53376)

H&E staining was also analyzed in the hippocampal area. Starting at coordinates AP −1.7 mm and ending AP −3.9 mm from bregma, coronal brain sections (30 μm) covering the whole dorsal hippocampus. A total number of six sections per rat were used. Cells presenting with nuclear and cytoplasmic staining (H&E) were manually counted in the CA3 neurons. CA3 cell counting spanned the whole CA3 area, starting from the end of hilar neurons to the beginning of curvature of the CA2 region in both the ipsilateral and contralateral sides. Sections were examined with Nikon Eclipse 600 microscope at 20×. All data are represented as mean±SEM values, with statistical significance set at $p<0.05$.

Measurement of Cell Survival: Human Nuclei Staining Analysis.

Every sixth 30-μm-thick coronal tissue section of brain and spleen, spanning the area of injury in the case of the brain and the entire red pulp in the case of spleen were randomly selected for quantitative analysis. Free-floating sections were washed three times for 5 min in PBS. For human nuclei (HuNu) staining, samples were blocked for 60 min at room temperature with 5% normal goat serum (Invitrogen) in PBS containing 0.1% Tween 20 (PBST; Sigma). Sections were then incubated overnight at 4° C. with mouse monoclonal anti-HuNu (1:50; MAB1281; Millipore) with 5% normal goat serum. The sections were washed five times for 10 min in PBST and then soaked in 5% normal goat serum in PBST containing corresponding secondary antibodies, goat anti-mouse IgG Alexa Fluor 488 (green; 1:500; Invitrogen), for 90 min. Finally, sections were washed five times for 10 min in PBST and three times for 5 min in PBS, then processed for Hoechst 33258 (bisBenzimideH 33258 trihydrochloride; Sigma) for 30 min, washed in PBS, and cover slipped with Fluoromount (Sigma). Brain and spleen sections were examined using a confocal microscope (Olympus). Control studies included exclusion of primary antibody substituted with 5% normal goat serum in PBS. No immunoreactivity was observed in these controls.

Flow cytometry.

Immunophenotypical analysis of cultured cells was performed using FITC-, phycoerythrin-, or adenomatous polyposis coliconjugated monoclonal antibodies against CD31, CD34, CD44, CD45, CD73, CD90, CD105, CD106, and CD117 and appropriate isotype controls.

Cells were detached using TryLE Select (Invitrogen), washed, and resuspended at a concentration of 106 cells/ml. Cells were incubated at 4° C. for 10 min in PBS with 10% FBS. Cells were centrifuged for 5 min at 1200 rpm. The cell pellet was resuspended in the binding buffer (PBS/2% FBS/0.01% sodium azide), followed by incubation with optimized concentrations of specific mAbs at 4° C. for 30 min, then washed with the binding buffer, resuspended in 0.5 ml of the same buffer, and analyzed within 1 h using the BD Accuri C6 flow cytometer (BD Biosciences).

Statistical Analyses.

The data were evaluated statistically using either two-way ANOVA or repeated-measures ANOVA and subsequent post hoc Scheffe's or Bonferroni's test for behavior. Statistical significance was preset at $p<0.05$.

CONCLUSION

The results suggest that hADSC cell transplantation and CM from hADSCs have the potential to boost endogenous repair mechanisms as observed in the ability to improve motor and cognitive behaviors, as well as prevention of cortical and hippocampal damage. The inventors demonstrate two major findings. First, lncRNA found in exosomes secreted by hADSCs plays a major role in the efficacy of the CM and, by extrapolation, plays a role in the actions of the transplanted hADSCs. Second, in aged rats, there is a decreased efficacy of the hADSCs and CM, and the inventors propose that this is related to the reduced migration of hADSCs and/or reduced survival of hADSCs in the aged groups and potentially reduced migration of exosomes carrying lncRNA to the spleen. These findings directly advance the basic scientific knowledge about a potent mechanism of brain repair in TBI and provide pivotal guidance into the translational applications of cell therapy to TBI patients.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of treating traumatic brain injury in a patient in need thereof comprising administering a therapeutically effective amount of long non-coding RNAs (lncRNAs) to the patient wherein the lncRNAs are nuclear enriched abundant transcript 1 (NEAT1) and metastasis associated lung adenocarcinoma transcript 1 (MALAT1), wherein the lncRNAs are administered in adipose-derived stem cells (ADSCs) lacking endothelial markers or conditioned media from cultured ADSCs.

2. The method of claim 1, wherein the ADSCs are administered to the patient intravenously.

3. A method of improving cognition in a patient having traumatic brain injury comprising administering a therapeutically effective amount of lncRNAs to the patient wherein the lncRNAs are NEAT1 and MALAT1, wherein the lncRNAs are administered to the patient intravenously in ADSCs lacking endothelial markers or conditioned media from cultured ADSCs.

4. A method of inducing neuroprotection in a patient having a traumatic brain injury comprising administering a therapeutically effective amount of lncRNAs to the patient wherein the lncRNAs are NEAT1 and MALAT1, wherein the lncRNAs are administered in ADSCs lacking endothelial markers or conditioned media from cultured ADSCs.

5. The method of claim 4, wherein the ADSCs are administered to the patient intravenously.

* * * * *